(12) United States Patent
Strauss

(10) Patent No.: US 7,721,349 B1
(45) Date of Patent: May 25, 2010

(54) FLEXIBLE PERSONAL EVAPORATIVE COOLING SYSTEM WITH WARMING POTENTIAL

(76) Inventor: Ted Nathan Strauss, P.O. Box 1402, Nevada City, CA (US) 95959

( * ) Notice: Subject to any disclaimer, the term of this patent is extended or adjusted under 35 U.S.C. 154(b) by 1039 days.

(21) Appl. No.: 11/166,675

(22) Filed: Jun. 25, 2005

(51) Int. Cl.
*A42B 1/00* (2006.01)
*A61F 9/00* (2006.01)

(52) U.S. Cl. ............... 2/7; 2/160; 2/102; 2/69; 2/81; 62/259.3; 450/36; 450/37; 450/38

(58) Field of Classification Search ............... 62/259.3; 2/160, 102, 69, 7, 81; 450/36–38
See application file for complete search history.

(56) References Cited

U.S. PATENT DOCUMENTS

| | | | | |
|---|---|---|---|---|
| 2,875,447 A | * | 3/1959 | Goldmerstein | 2/209.3 |
| 3,125,865 A | * | 3/1964 | Bemelman | 62/259.3 |
| 4,451,934 A | * | 6/1984 | Gioello | 2/113 |
| 5,157,788 A | * | 10/1992 | Schultz | 2/7 |

* cited by examiner

*Primary Examiner*—Frantz F. Jules
*Assistant Examiner*—Azim Rahim

(57) ABSTRACT

A system for cooling the skin of a human or animal user includes thermally conductive elements (120) with fluid-wicking surfaces (124), ways to flexibly interconnect the elements, methods for storing a cooling fluid and distributing it to elements (120), and ways to maintain elements (120) in contact with a user's skin. When at least portions of the elements (120) are in contact with a user's skin and at least portions of the element surfaces are wet with fluid, the evaporation of fluid from the surfaces transports heat from the user's skin into the surrounding air, thereby cooling the user. More powerful embodiments further include an air space (165) parallel and adjacent to the user's skin into which elements (120) penetrate, and a fan for moving air through the air space (165), thereby speeding the evaporation of fluid from the surfaces of the elements (120). Thermostatic or electronic means can be added to control the fan, thereby automatically cooling the user when the fan activated, and warming the user when the fan is deactivated by using the materials and air spaces in the device as thermal insulation.

8 Claims, 32 Drawing Sheets

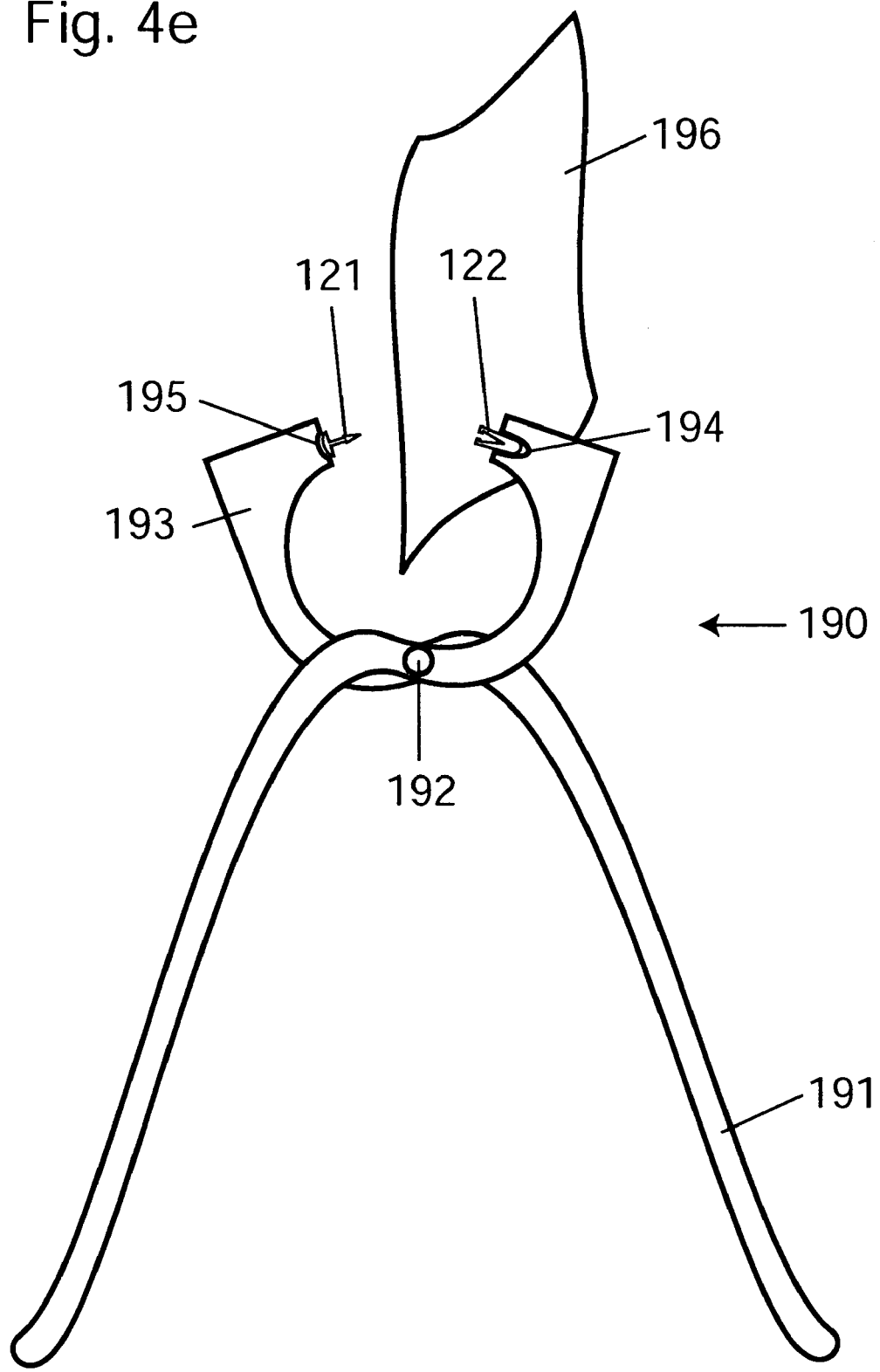

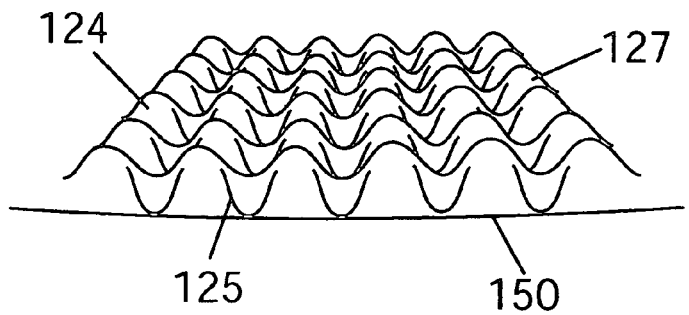
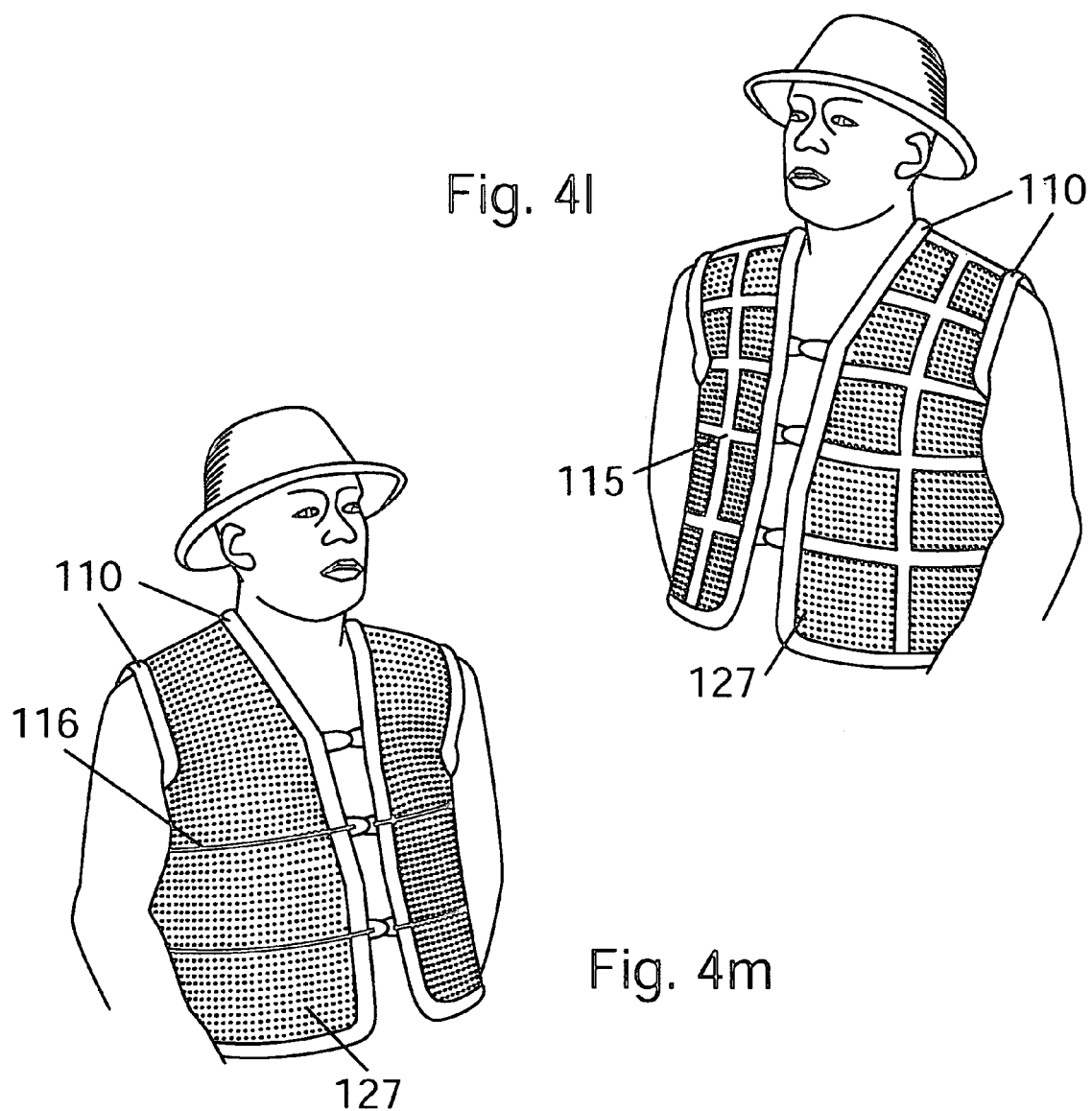
Fig. 4k
Fig. 4l
Fig. 4m

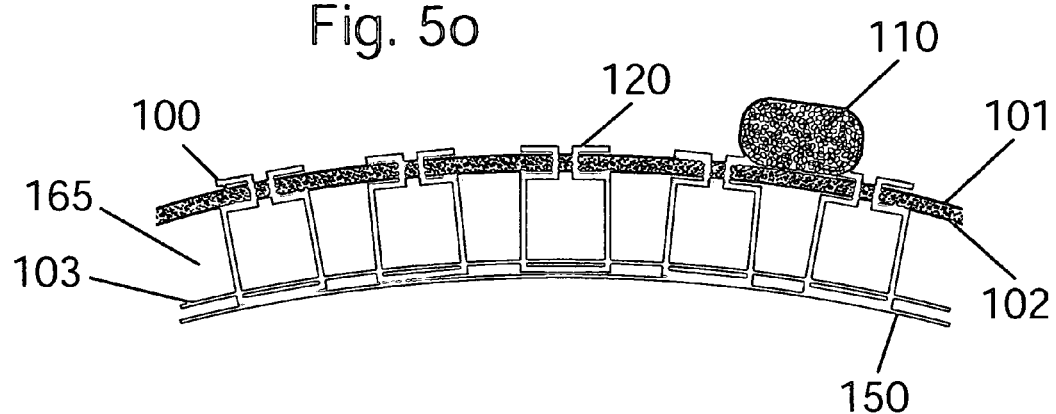
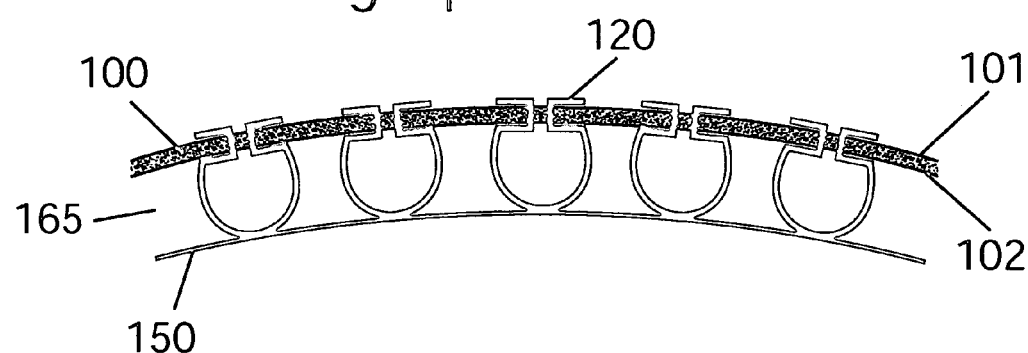
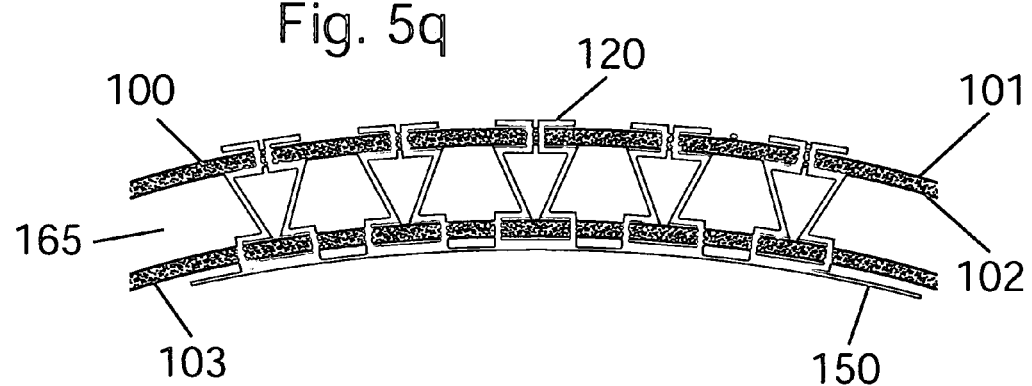

FLEXIBLE PERSONAL EVAPORATIVE COOLING SYSTEM WITH WARMING POTENTIAL

BACKGROUND

1. Field of Invention

This invention relates to the field of personal comfort devices, specifically, evaporative personal cooling devices that can be worn by humans or animals.

2. Prior Art

Throughout history, people have used various methods in attempts to keep themselves cool on hot days and in hot environments, especially when engaged in strenuous activities. Simple methods of personal cooling include wearing a moistened bandanna around one's neck, shading oneself with a hat or parasol, manually fanning oneself, using portable fans and/or misting devices, wetting or removing one's clothing, and changing into lighter clothing. All of these attempts have at least one of the following disadvantages:

- The user must hold a device or take some action to derive a benefit (which is not only bothersome but may be tiring and self defeating, since such activity can generate more internal heat than it dissipates).
- Removing clothing is often inappropriate or undesirable.
- Changing into lighter clothing is often inconvenient or inappropriate.
- Wetting the body and/or clothing can be uncomfortable, unaesthetic, or even embarrassing.
- They provide only short-term relief.
- They provide relatively ineffective cooling.
- They are impossible or impractical to implement when wearing heavy or protective clothing or equipment.
- They do not cover as large an area as needed.

With the development of modern technologies, new ways have been found to produce a portable cooling effect, including:

- Pumping cool gels or fluids through a vest or other garment
- Creating portable refrigerators with chlorofluorocarbon coolants
- Transferring coolness from a refrigerator or freezer to the body through liquids, gels, or solid materials
- Using compressed gas to create a stream of cool air or vapor across the skin
- Employing Peltier (thermoelectric) cells Still, each of these methods has serious drawbacks for the average user, due to cost, complexity, lack of portability, discomfort, difficulty of use, and/or lack of effectiveness. Most of these applications are ineffective because they require more energy than today's batteries can deliver beyond a brief period.

Because the evaporative cooling effect of water is simple and economical to harness, many personal evaporative cooling systems have been developed and refined over the years. U.S. Pat. Nos. 5,775,590 by Utter (Jul. 7, 1998) and 5,671,884 by Restive (Sep. 30, 1997) describe devices consisting of a portable water reservoir that, when pressurized by a user, propels water through a hose and out through a tiny nozzle, spraying the user with a fine water mist. By securing the device to the user's body with a belt or strap and by providing a clip that allows the user to direct the mist, these devices create a portable hands-free evaporative cooling effect. The disadvantages of this approach include: 1) the effect is very localized, 2) they wet the user's body and clothing, 3) they require the user to manually pressurize the bottle at intervals, 4) they require the user to move the nozzle to cool other areas of the body, and 5) because they do not use a fan, the cooling effect is minimal and inconsistent (a breeze is necessary for maximum effectiveness).

In an attempt to provide the needed moving air, there are a number of devices that allow the user to mist himself or herself while also employing a fan to move air across the moistened skin. U.S. Pat. No. 5,667,731 by Junket, et al. (Sep. 16, 1997) discloses a combination spray bottle and fan. It allows the user to spray himself with water while simultaneously directing the fan across the dampened skin. While this device makes up for the lack of moving air in the previously mentioned devices, it suffers from the remaining disadvantages already mentioned and additionally requires the user to hold the bottle and squeeze the trigger at intervals.

My U.S. Pat. No. 5,802,865 (Sep. 8, 1998) discloses a cooler that uses a fan to evaporate water from a powder-coated heat sink within the device and delivers the resulting coolness to the neck or forehead of the user without requiring the user to hold anything, do anything, or get wet. However, because this device is not flexible, it must be made to fit specific neck or head sizes and is not appropriate for other applications. The lack of flexibility also prevents this device from being used on a larger area of the body, and therefore does not cool the user nearly as much as would be desirable.

U.S. Pat. No. 6,371,388 by Utter, et. al (Apr. 16, 2002) discloses a device is that is strapped to the front of a user's body, and blows air mixed with a water mist up the front of the user's body. This approach has several disadvantages: 1) it wets the user's shirt, 2) because it blows over the user's shirt, it has little effect on cooling the user's torso, 3) it destroys the user's hairdo, 4) it requires the user to manually trigger the water spray, and 5) it is bulky, unattractive, and relatively expensive.

My U.S. Pat. No. 6,543,247 (Apr. 8, 2003) discloses a device that is strapped to the front or rear of a user's body and blows air mixed with a water mist up the front or back of a user's body under his or her shirt or blouse. This approach has the advantages of not wetting the user's clothes and, because the air/water stream is moving directly against the skin, produces a reasonable cooling effect over a larger area than most evaporative cooling devices. But this technique still has certain disadvantages, such as: 1) it does not cool the torso as much as desired, 2) it wets the user's skin, 3) inexpensive embodiments require the user to trigger the water spray manually, 4) it cannot cool the back of a hiker wearing a backpack, and 5) it cannot cool users who are wearing motorcycle leathers, protective suits, or tightly fitting clothing.

U.S. Pat. No. 6,257,011 by Siman-Tov, et al. (Jul. 10, 2001) reveals a portable lightweight cooling garment having a channeled sheet that absorbs sweat and/or evaporative liquid, a layer of highly conductive fibers adjacent to the channeled sheet and a device for moving air through the sheet. U.S. Pat. No. 6,134,714 by Uglene (Oct. 24, 2000) discloses a personal cooling garment with inner and outer layers defining a confined space for containing liquid that can evaporate to create a cooling effect. The drawback of both approaches is that they do not increase the surface area beyond what is provided by the user's skin, and therefore can only make the evaporative cooling effect somewhat more consistent, but not more cooling than perspiring on a breezy day.

U.S. Pat. No. 5,755,110 by Silvas (May 26, 1998) describes a cooling vest having a plurality of elongated pocket partitions containing beads of polyacrylamide. These absorb liquid to form a gel that may be chilled or frozen to provide a cooling effect on the upper torso of a human wearer. The problem in all such approaches is that the cooling effect is neither as strong as desired nor as long-lasting as users would wish.

OBJECTS AND ADVANTAGES

Accordingly, several objects and advantages of the present invention are to provide an improved evaporative personal cooling device that:

1. Is smooth and flexible, therefore comfortable when worn against a user's body.
2. Can be made and sold inexpensively.
3. Is lightweight and unobtrusive.
4. Delivers a powerful evaporative cooling effect directly to the user's skin.
5. Offers long-term cooling relief.
6. Does not require the user to hold the device.
7. Requires the user to do little or nothing to enjoy its benefits.
8. Does not need to wet the user's skin or clothing.
9. Requires little or no battery power to run.
10. Would be useful for those who are relatively inactive, as well as those engaged in walking, jogging, or active sports.
11. Can cool pets and other animals.
12. Can itself be made into and worn as clothing, uniforms, or protective garments.
13. Can be worn under a backpack, uniforms, motorcycle leathers or other heavy garments, helmets, protective gear, or ordinary clothes.
14. Can be embodied as clothing, accessories, or blankets.
15. Can be embodied as devices with adjustable warming/cooling potential.
16. Does not require the user to change clothing or add outerwear or accessories as the temperature cools off.
17. Can be automatically controlled with a thermostat to maintain a relatively constant skin temperature.

Further objects and advantages will become apparent from a consideration of the drawings and ensuing description.

SUMMARY

A system for cooling the skin of a human or animal user includes:

- A plurality of thermally conductive elements, each promoting fluid to wick across at least portions of its surface,
- A flexible hydrophilic fabric or sponge reservoir,
- Means for the conductive elements to be maintained in contact with the reservoir so that fluid will tend to migrate from the fabric onto and across element surfaces, and
- Means for maintaining one or more portions of the elements in physical or at least thermal contact with the user's skin, whereby when the fabric is wet, water has migrated onto the elements, and one or more portions of the elements are in contact with the user's skin, heat from the user's skin is transferred through the elements to the evaporating fluid and into the surrounding air, cooling the user. By adding an air space adjacent and parallel to the user's skin into which the elements penetrate, along with means to move air through the air space, the device is made more powerful. By adding thermostatic control means, the device can be embodied as automatic temperature-regulating clothing.

DRAWING FIGURES

FIG. 2l shows a fan-free embodiment for cooling a dog.

Figure 4A:
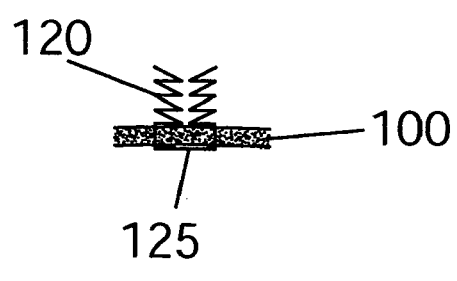
FIG. 4a shows an edge view of an element having an alternate shape
Figure 4B:
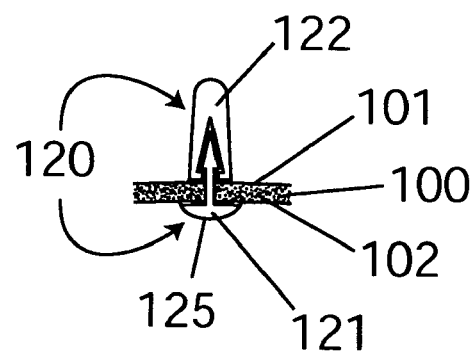
FIG. 4b shows a snap-together two-part element.
Figure 4C:
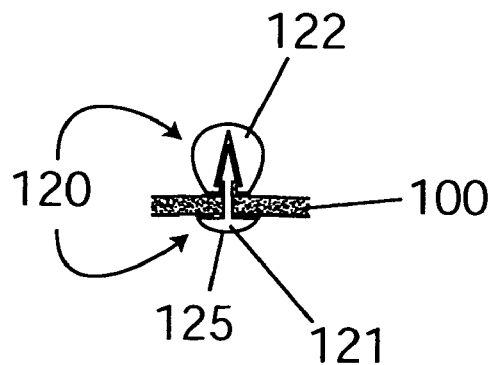
FIG. 4c shows a snap-together two-part element with a spherical top.
Figure 4D:
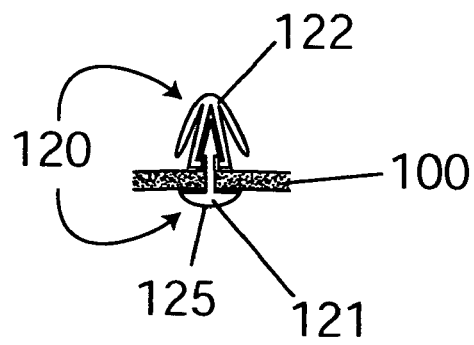
FIG. 4d shows a snap-together two-part element with extra surface area.
Figure 4F:
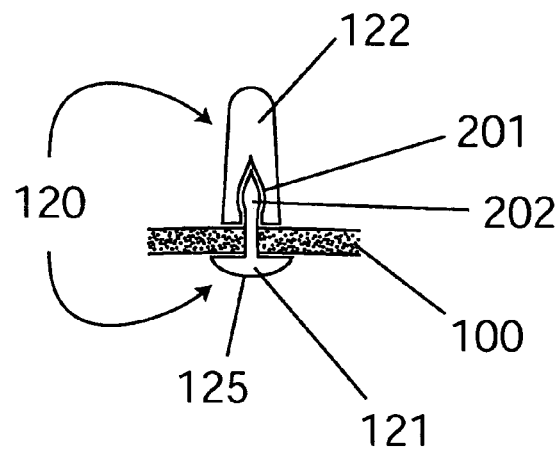
FIG. 4f shows a two-part removable snap-together system.
Figure 4G:
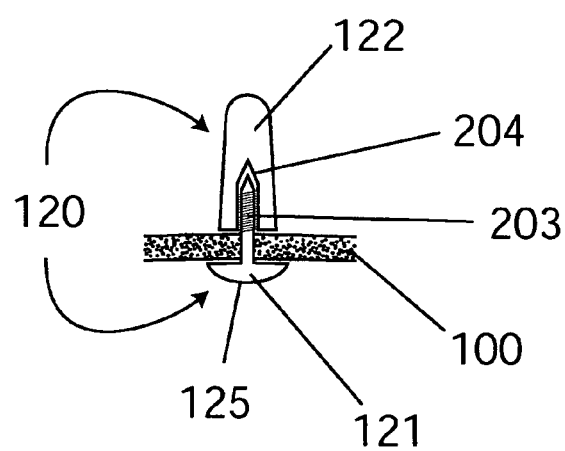
FIG. 4g shows a two-part removable screw-together system.
Figure 4H:
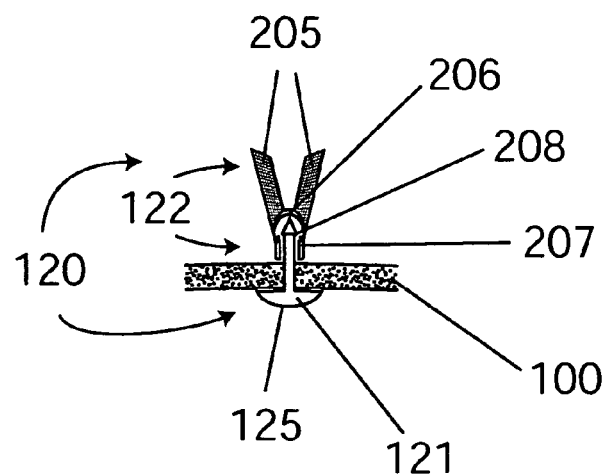
FIG. 4h shows a two-part removable clip-together system.
Figure 4I:
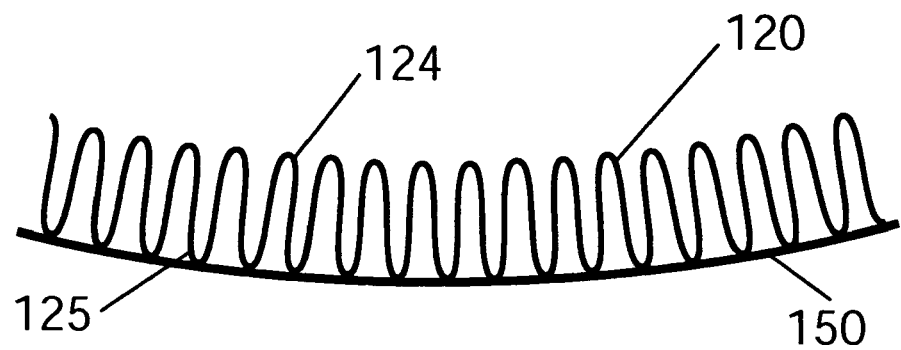
FIG. 4i shows an edge view of a corrugated element strip.
Figure 4J:
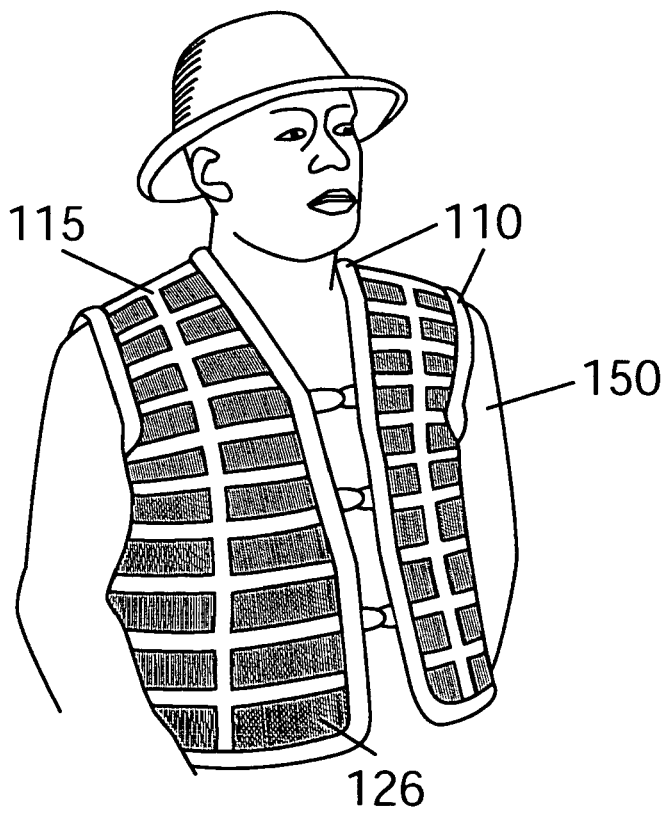
FIG. 4j shows corrugated element strips used in a vest embodiment.
Figure 4N:
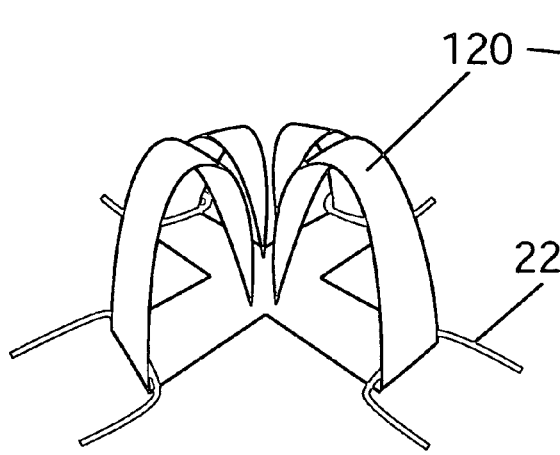
FIG. 4n is a close-up perspective view of a 4-pronged element with elastic connectors.
Figure 4O:
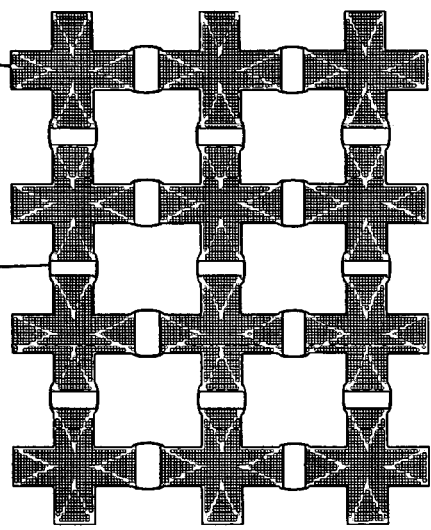
FIG. 4e shows a special tool for inserting two-part elements into existing articles.
FIG. 4k shows a perspective view of an egg-crate deformed element.
FIG. 4l shows a vest embodiment using several egg-crate deformed elements.
FIG. 4m shows a vest embodiment using a single egg-crate deformed element.

FIG. 4*o* is a top view of a group of 4-pronged elements connected together.

Figure 4P:
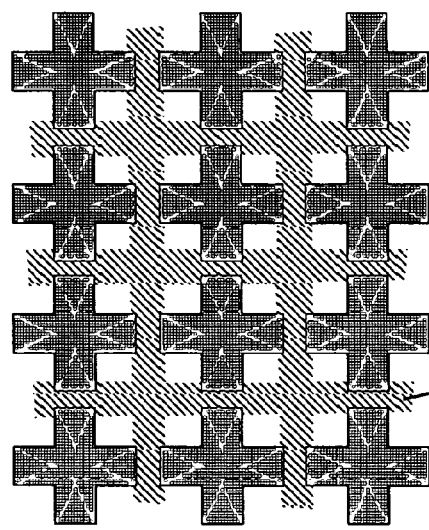

FIG. 4*p* shows a group of 4-pronged elements connected using an elastic fabric.

Figure 4Q:
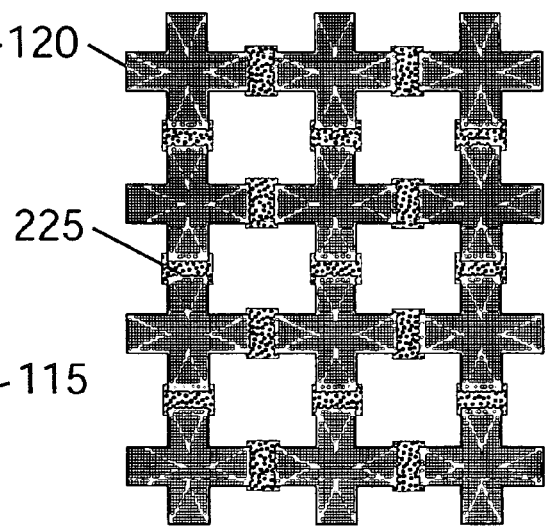

FIG. 4*q* shows a group of elements connected using elastic, fluid-wicking parts.

Figure 5A:
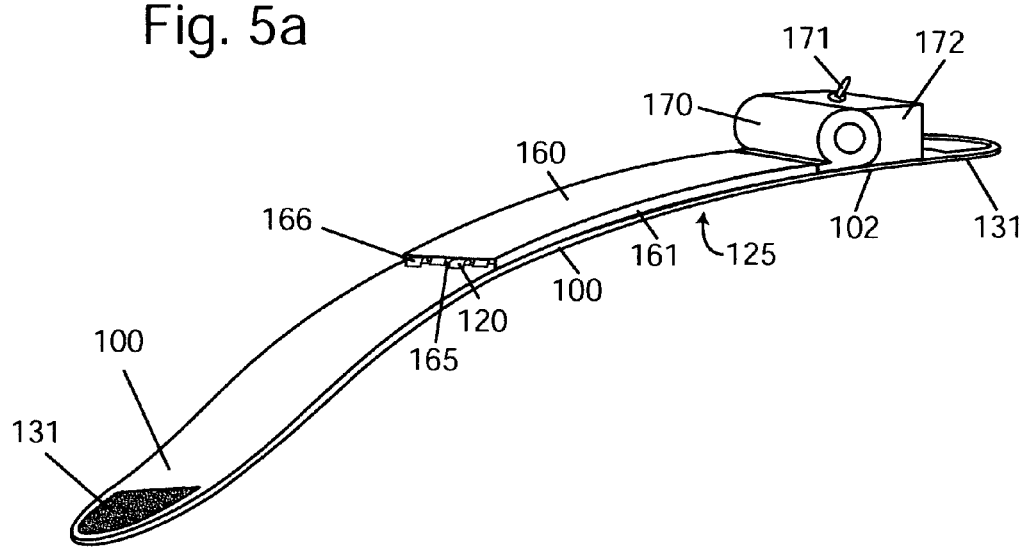

FIG. 5*a* shows a forced air headband embodiment not being worn.

Figure 5B:
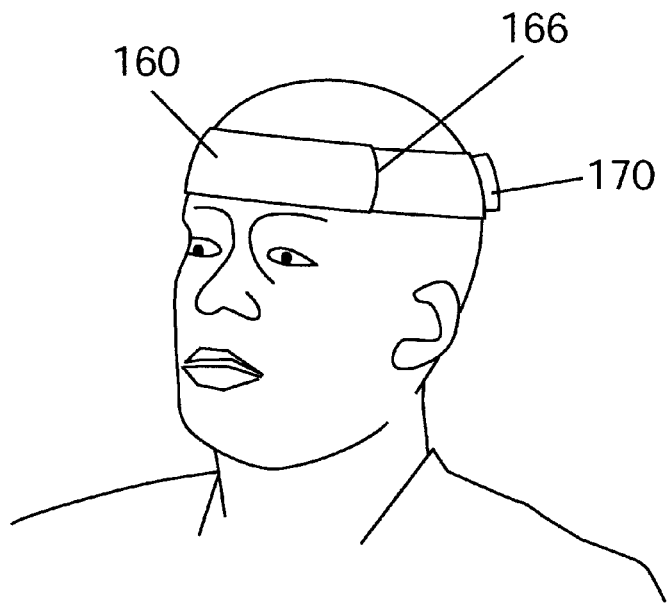

FIG. 5*b* shows a user wearing a forced air headband embodiment.

Figure 5C:
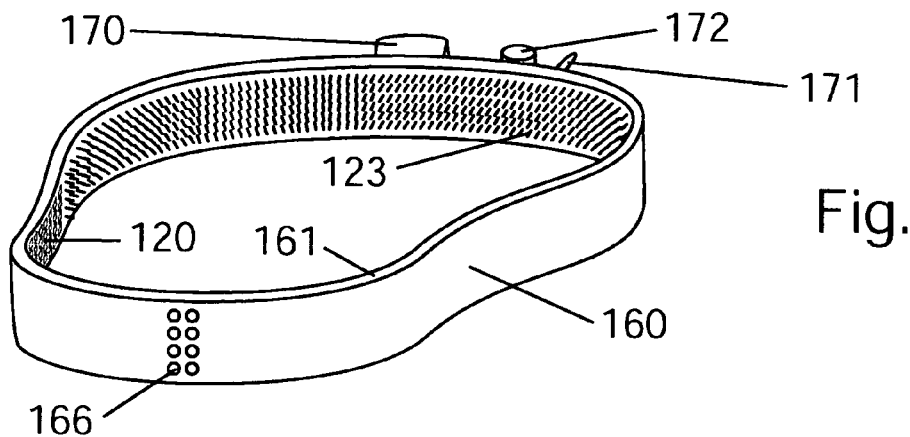

FIG. 5*c* shows a forced air embodiment for cooling the forehead and the scalp.

Figure 5D:
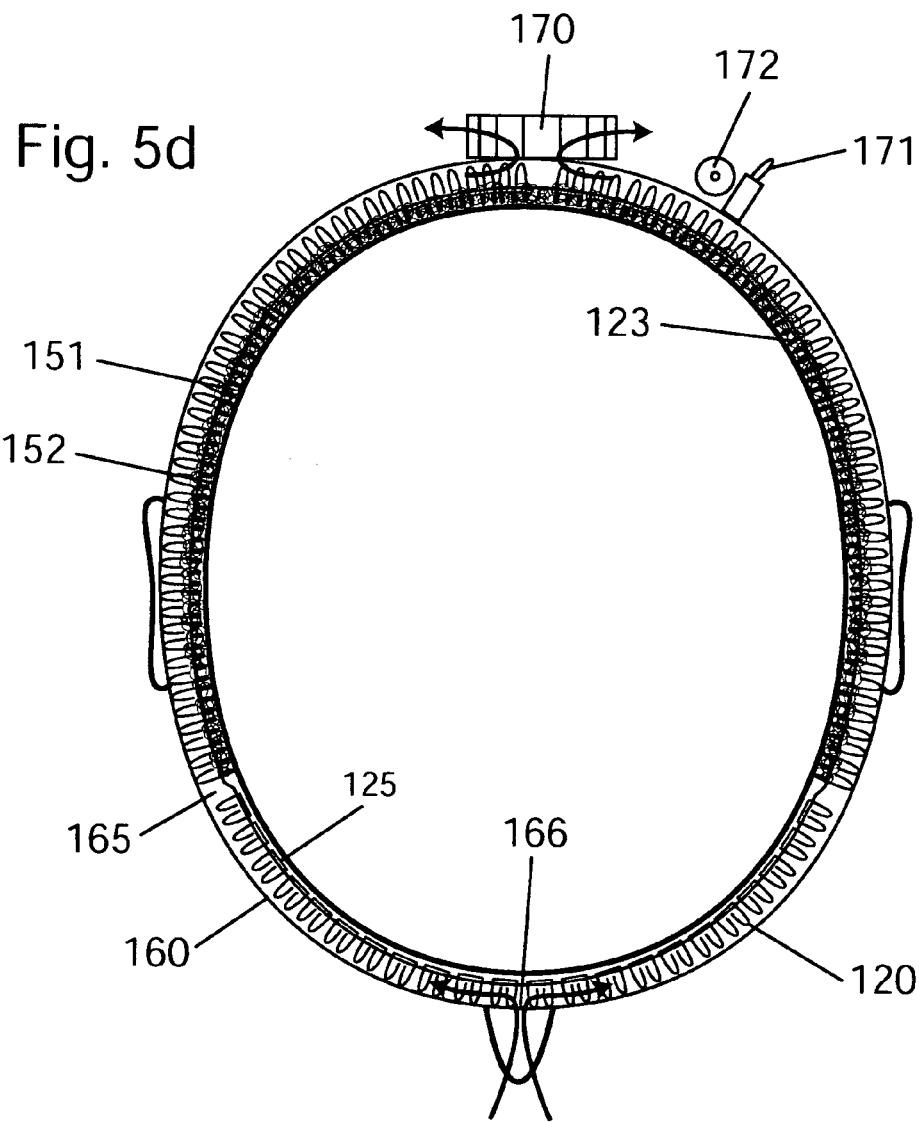

FIG. 5*d* is a top view of a user wearing the device of FIG. 5*c*.

Figure 5E:
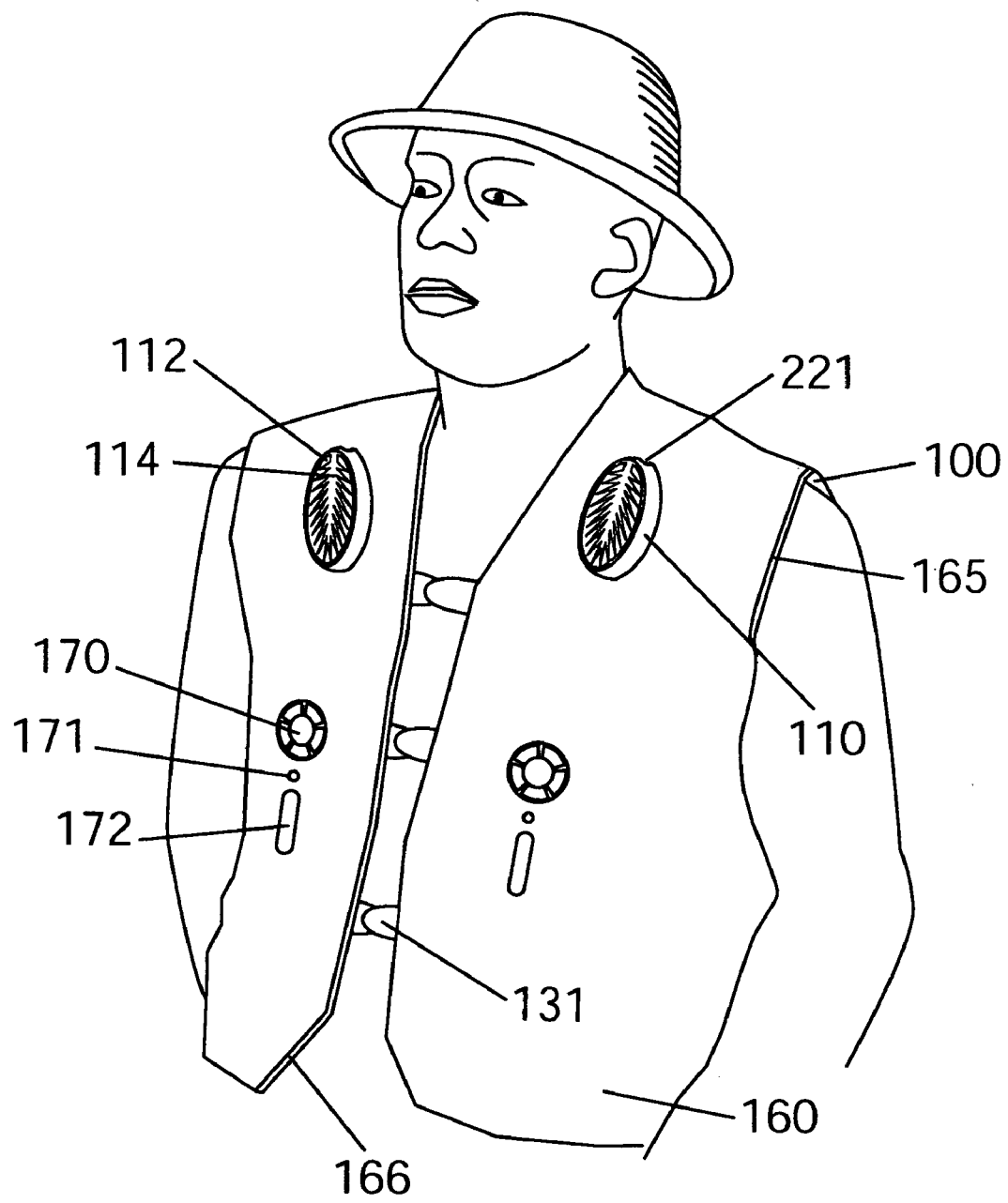

FIG. 5*e* shows a user wearing a forced air vest embodiment.

Figure 5F:
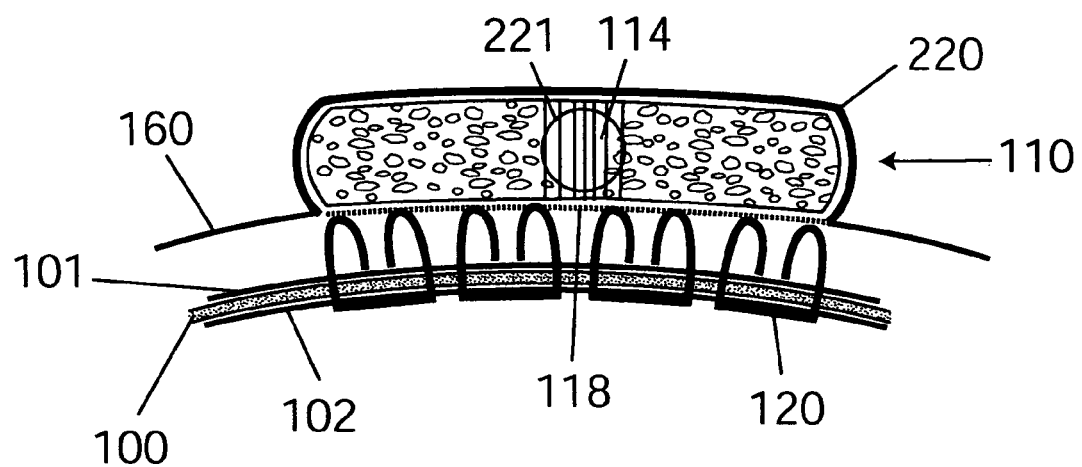

FIG. 5*f* shows an additional reservoir sitting on elements in a forced air embodiment.

Figure 5G:
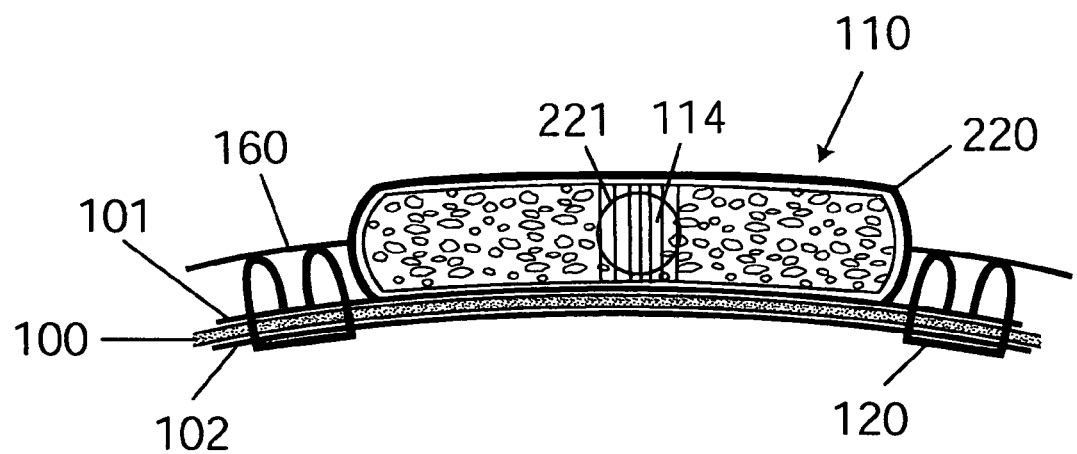

FIG. 5*g* shows an additional reservoir sitting on the primary reservoir in a forced air embodiment.

Figure 5H:
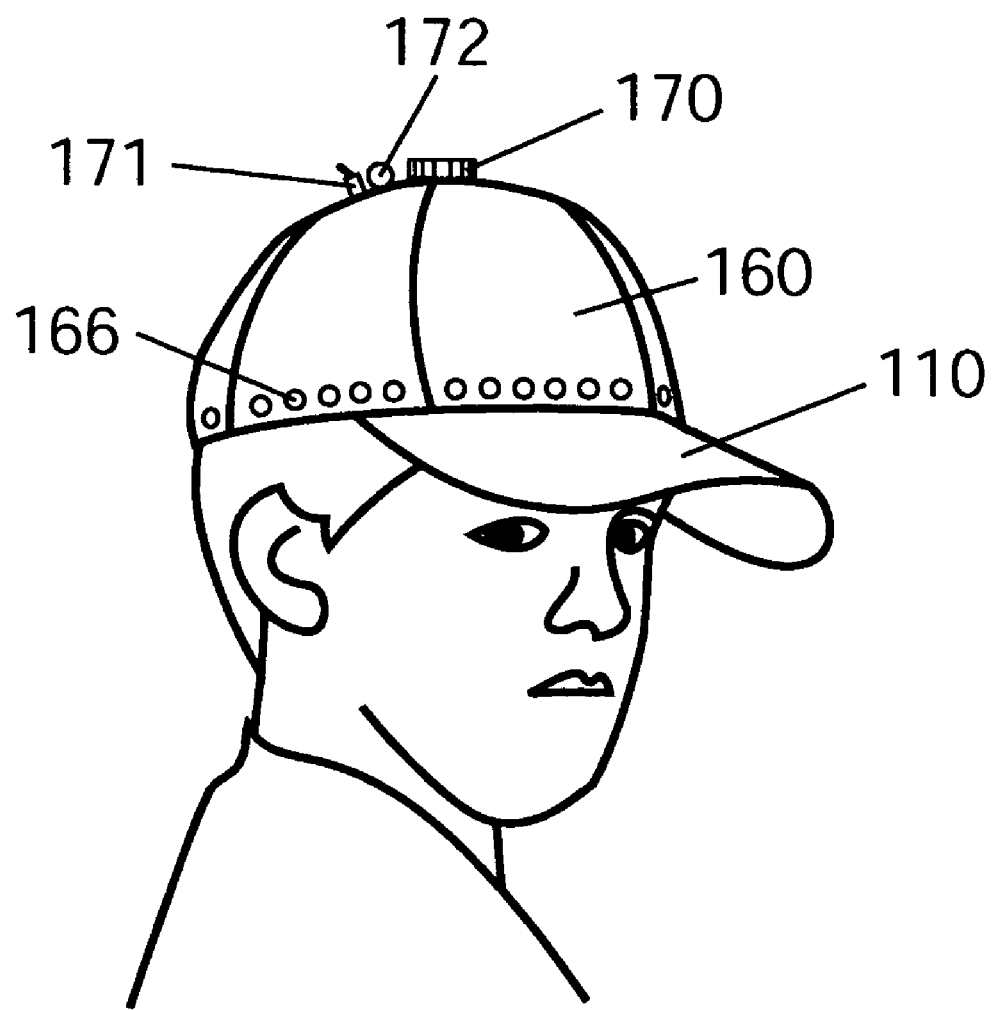

FIG. 5*h* shows a forced air baseball cap embodiment.

Figure 5I:
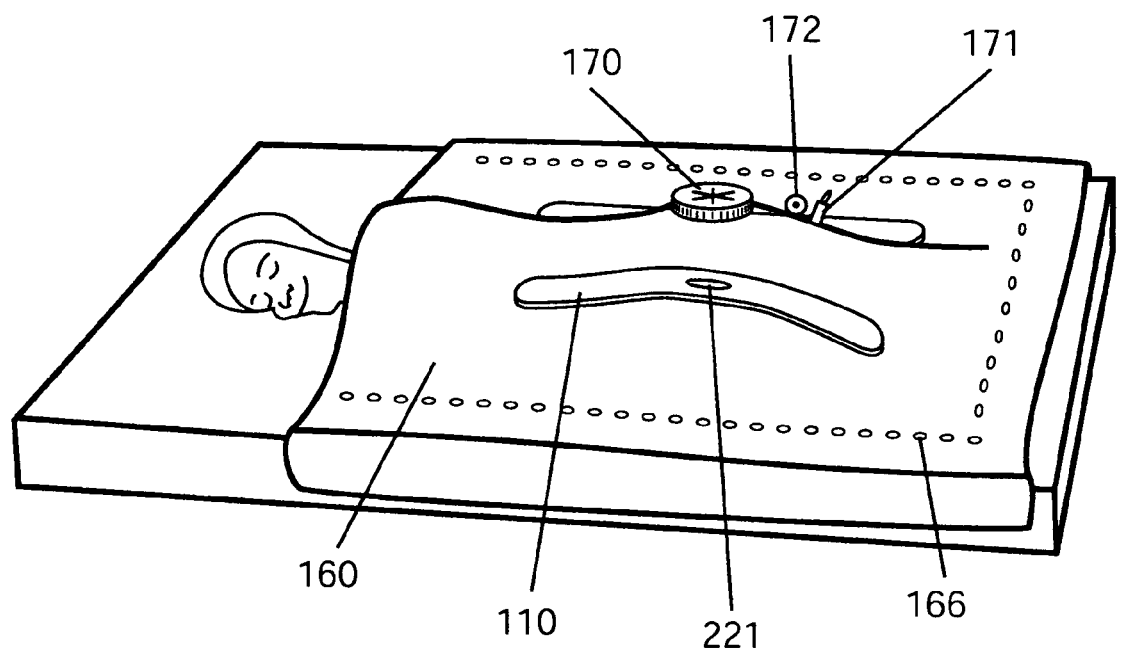

FIG. 5*i* shows a forced-air cooling blanket embodiment.

Figure 5J:
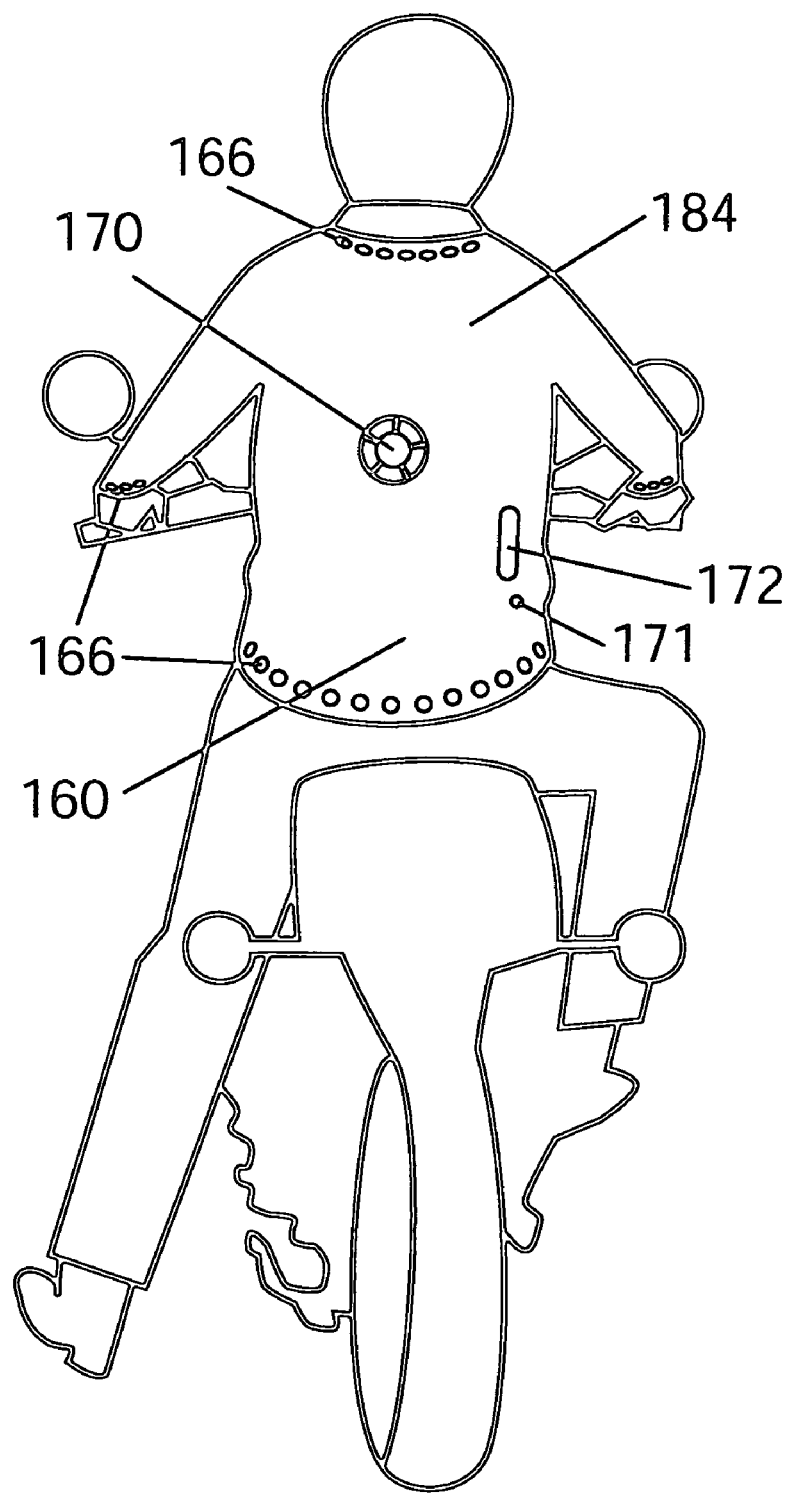

FIG. 5*j* shows a forced-air motorcycle jacket embodiment.

Figure 5K:
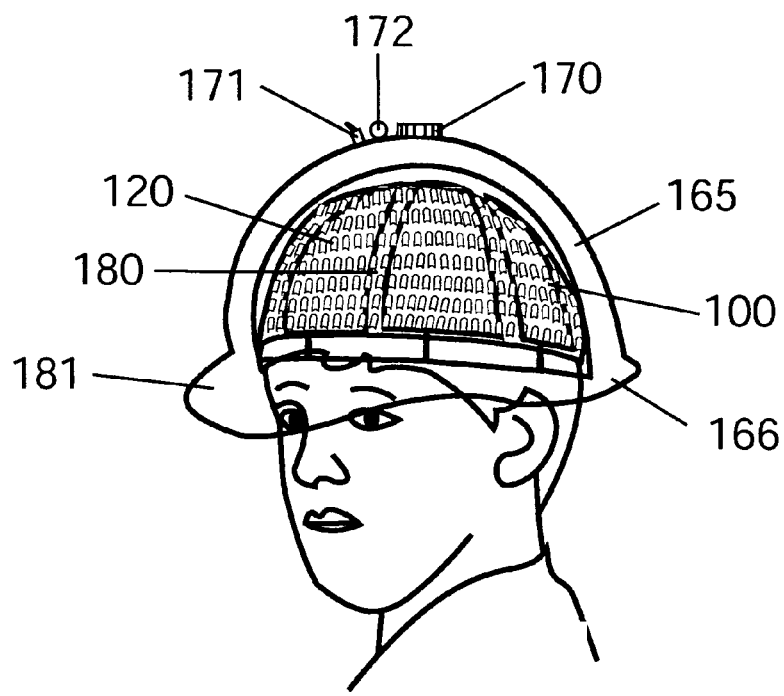

FIG. 5*k* shows a forced air hard hat embodiment.

Figure 5L:
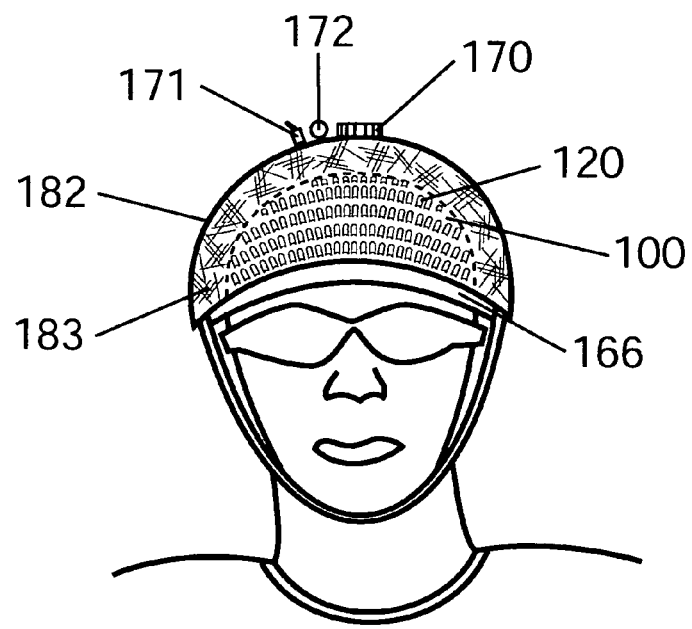

FIG. 5*l* shows a forced air motorcycle helmet embodiment.

Figure 5M:
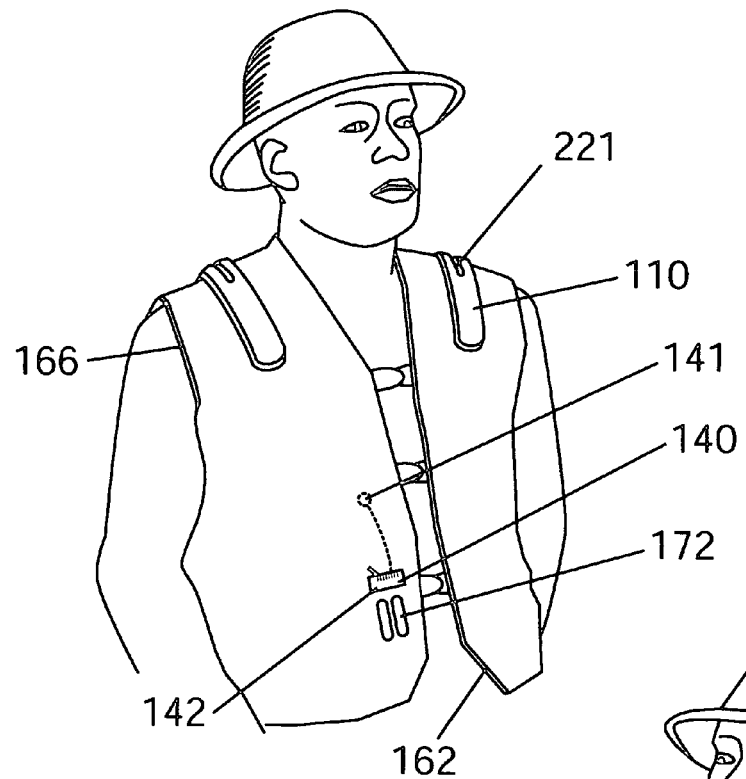

FIG. 5*m* shows a thermostatically controlled forced-air vest embodiment.

Figure 5N:
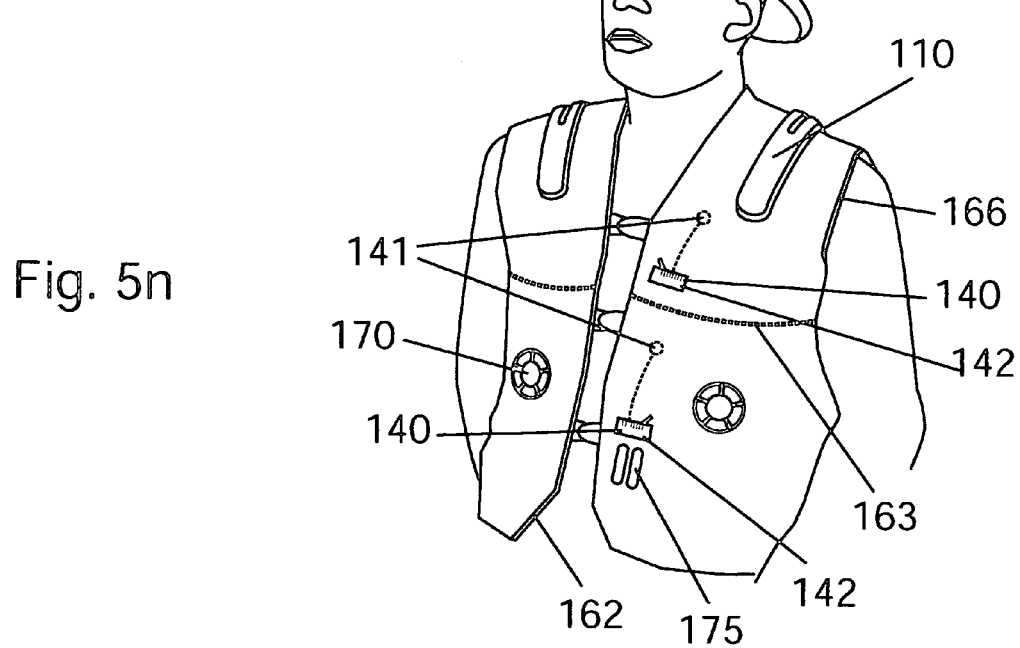

FIG. 5*n* shows a thermostatically controlled embodiment with multiple zones.

FIG. 5*o* shows the primary reservoir on top of the cooling elements.

FIG. 5*p* shows primary reservoir on top of the cooling elements with rounded element bottoms.

FIG. 5*q* shows primary reservoir at both the top and the bottom of the cooling elements.

Figure 6A:
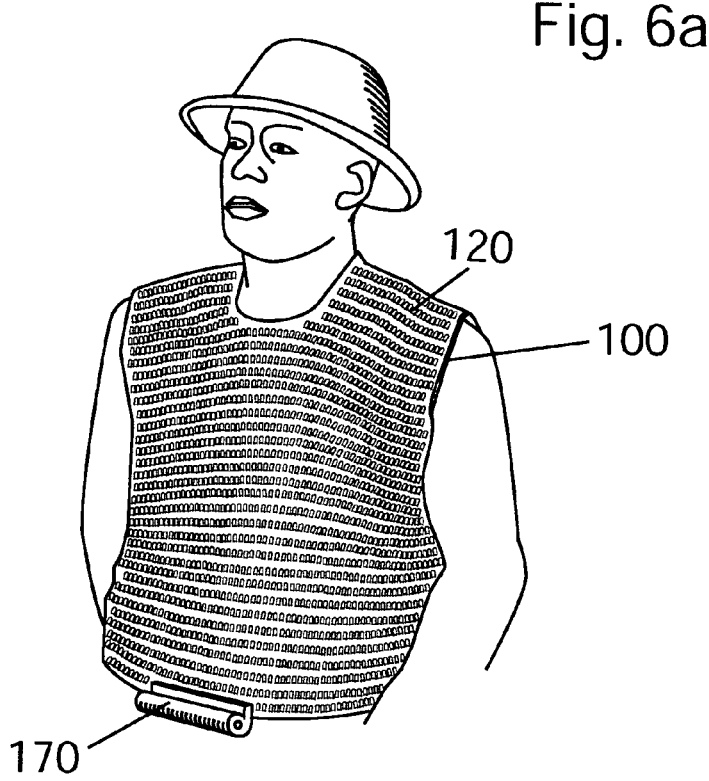

FIG. 6*a* shows a forced air shirt embodiment designed to be used under an existing T-shirt.

Figure 6B:
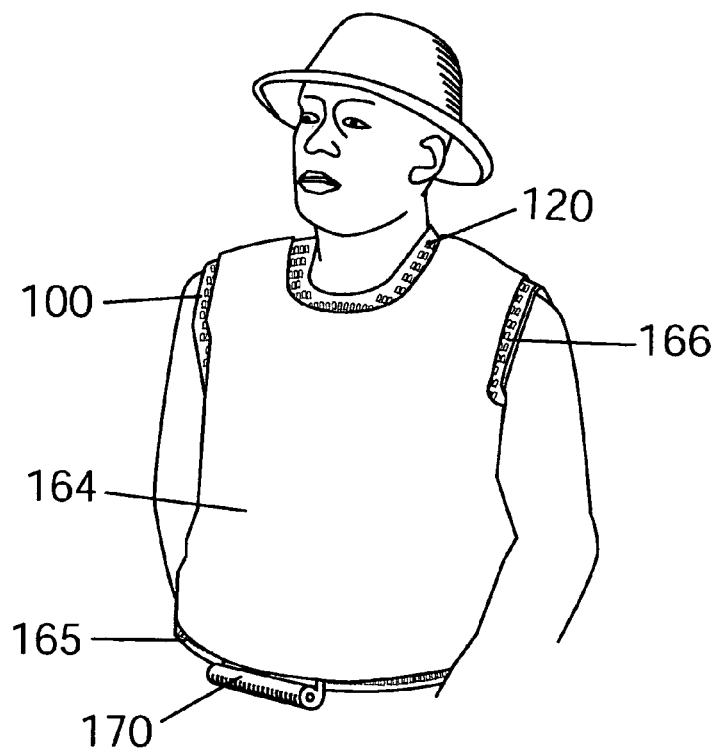

FIG. 6*b* shows the device in FIG. 6*a* with existing T-shirt in place.

Figure 6C:
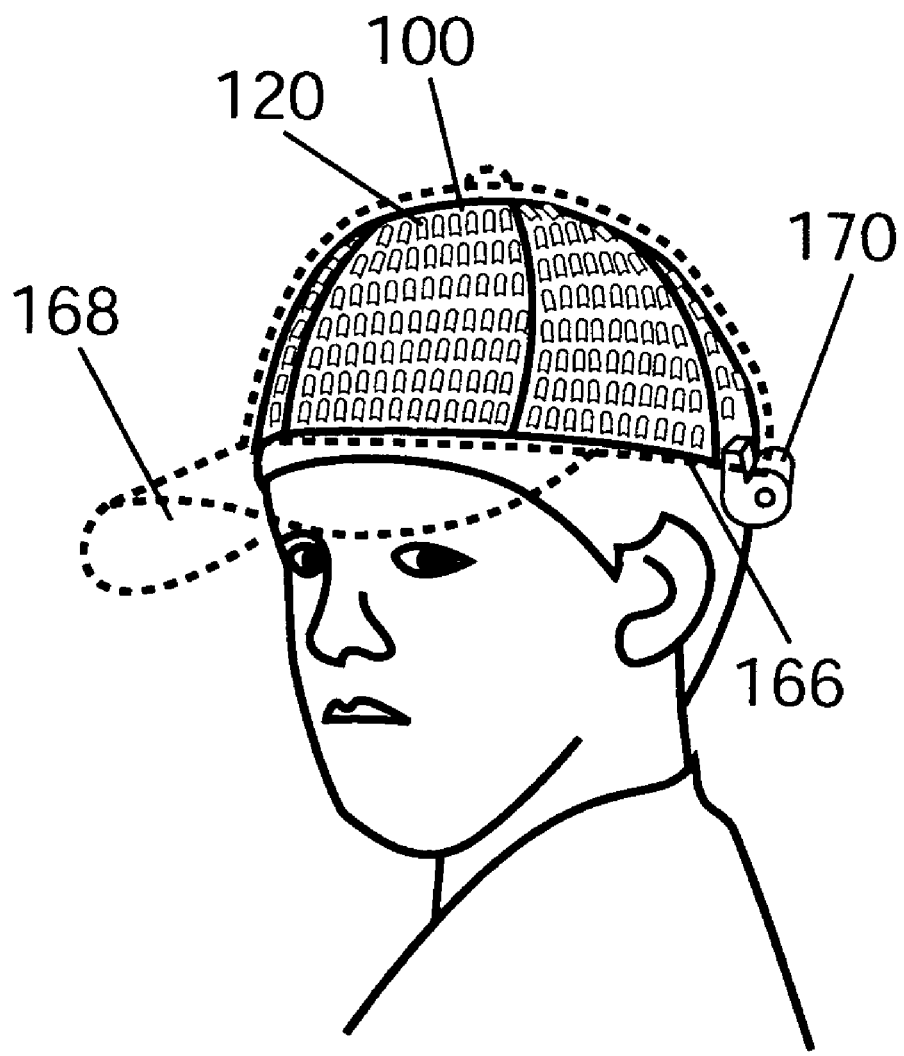

FIG. 6*c* shows an embodiment designed to be worn under an existing baseball cap.

REFERENCE NUMERALS

| 100 | primary reservoir |
| 101 | outer reservoir barrier |
| 102 | inner reservoir barrier |
| 103 | stabilizing fabric |
| 104 | slits |
| 105 | device edges |
| 109 | external reservoir |
| 110 | additional reservoir |
| 111 | water line |
| 112 | sponge |
| 113 | reservoir cap |
| 114 | notch |
| 115 | elastic fabric |
| 116 | elastic belts |
| 117 | holes |
| 118 | wicking material |
| 119 | sponge holder |
| 120 | elements |
| 121 | bottom element part |
| 122 | top element part |
| 123 | cooling element extensions |
| 124 | fluid-wicking surface |
| 125 | skin-facing surface |
| 126 | 2-D corrugated element strips |

-continued

| 127 | 3-D corrugated elements |
| 131 | hook-and-loop fasteners |
| 140 | thermostat |
| 141 | temperature sensor |
| 142 | control circuit |
| 150 | user's skin |
| 151 | user's hair |
| 152 | user's scalp |
| 160 | outer air barrier |
| 161 | permanent edge air barrier |
| 162 | controllable edge air barriers |
| 163 | internal air barrier |
| 164 | existing article |
| 165 | air space |
| 166 | air intake vents |
| 167 | existing T-shirt |
| 168 | existing cap |
| 170 | fan |
| 171 | switch |
| 172 | battery |
| 180 | suspension straps |
| 181 | hard hat |
| 182 | Motorcycle helmet |
| 183 | foam padding |
| 184 | motorcycle jacket shell |
| 190 | snap tool |
| 191 | lever arms |
| 192 | pivot point |
| 193 | jaws |
| 194 | holder for element top |
| 195 | holder for element bottom |
| 201 | male snap shape |
| 202 | female snap shape |
| 203 | male threaded stud |
| 204 | female threaded socket |
| 205 | fluid-wicking fins |
| 206 | "C" spring |
| 207 | clip jaws |
| 208 | protruding ridge |
| 220 | reservoir cover |
| 221 | reservoir opening |
| 222 | reservoir bottom |
| 223 | element-free zone |
| 225 | elastic connectors |

Overview of the Cooling System and its Three Primary Expressions

My personal cooling system combines a unique, flexible heat sink with a method of maximizing the evaporative cooling effect. There are three basic expressions of the system, each of which has many possible embodiments:

1. Fan-free embodiments: Devices that rely on passive evaporation.
2. Integrated forced air embodiments: Devices that use one or more fans to speed evaporation and provide an integrated external air barrier to contain airflow.
3. Forced air embodiments for use with existing articles: Devices that use one or more fans and use an existing accessory or article of clothing as the external air barrier.

Fan-free embodiments are the simplest; all other expressions start there and provide additional features and benefits.

Expression #1

General Description of Fan-Free Embodiments

Figure 1A:
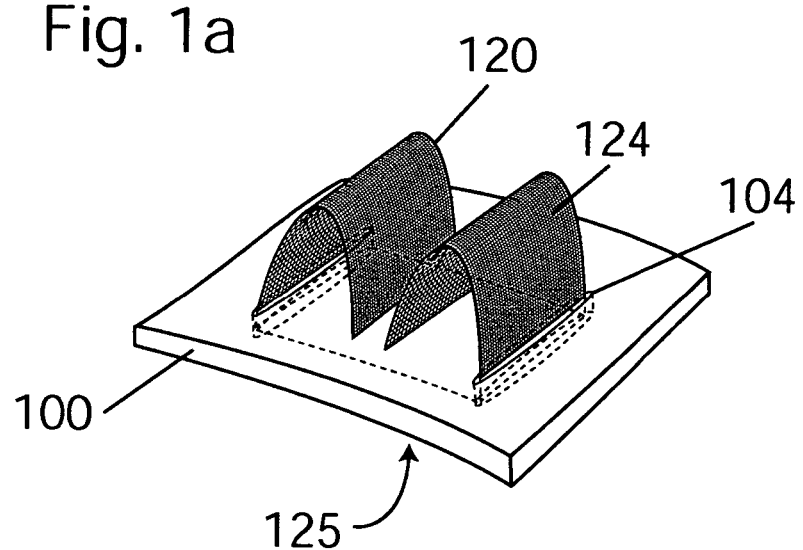
FIG. 1a is close-up view of a cooling element penetrating a primary reservoir.

Referring to FIG. 1*a*, the most basic fan-free embodiment of this cooling system requires only four components:

1. Thermally conductive elements 120 with fluid-wicking surfaces 124,
2. A way to flexibly interconnect the elements, such as with a flexible fabric primary reservoir 100, 3. A way to wet elements 120, and
4. A way to maintain at least portions of the elements in contact with a user's skin.

I've experimented with many approaches to maximizing the effectiveness of each ingredient and will mention in this section only the currently most favored solution; other approaches will be mentioned in the section titled "Embodiment #1: Alternative Methods".

Reservoir 100 is preferably made of a nylon/spandex or cotton/spandex fabric. Other materials that can be used include woven or nonwoven fabrics, foamed, porous, or laminated materials, etc. Reservoir 100 preferably provides a linear path for capillary action (vs. random path wicking provided by foamed materials) to effectively wick water vertically. Reservoir 100 not only wicks and holds water, but also provides a flexible backbone for the device.

One of the simplest and most effective ways I've found to flexibly interconnect elements 120 while simultaneously keeping them moist is by having elements 120 penetrate through slits 104 in an elastic, absorbent fabric that functions as reservoir 100 for water or other cooling fluid. When reservoir 100 is wet, water migrates onto fluid-wicking surfaces 124 of elements 120 and evaporates, transporting heat from elements 120 into the surrounding air.

Elements 120 are both thermally conductive throughout and fluid-wicking on at least portions of their surfaces. They are preferably formed of rectangles (heat sink radiation fins) of high-purity aluminum (for maximum heat transfer combined with low weight and cost), having dimensions of approximately twenty five thousandths of an inch thick by one quarter of an inch wide by one inch long. Each fin is formed into a square "U" shape, inserted through slits 104 in reservoir 100, and the two ends are curved toward each other and down toward the inside bottom of the "U", whereby element 120 mechanically attaches itself to reservoir 100 in the manner of a staple. This approach:

- Allows the fins to have sufficient length while taking little vertical space.
- Provides a large skin-facing surface 125 for cooling the user's skin.
- Allows each fin end to be supplied with fluid by wicking action from both locations where it touches reservoir 100 (at slits 104 and at both ends), effectively creating four fins from one piece.
- Permits elements 120 to be densely packed for maximum cooling effect.
- Attaches elements 120 to the fabric, thereby avoiding the need to use glue in the manufacturing process.
- Provides a softer look and feel on the outside of the device than if the fins ended either straight up or were bent down at an angle.

My experiments show that the most effective approach for promoting water to wick across surface 124 of elements 120 is to create a series of densely packed crosshatched grooves on both surfaces of each fin. The original aluminum sheet should first be mildly abraded, and the grooves should be approximately two and a half thousandths of an inch wide and at least the same in depth, and should be as close together as possible. Of the many ways to form such grooves, microdeformation using finning discs is currently the favored process because it is highly effective and inexpensive. FIG. 1a depicts fluid-wicking surface 124 of element 120 with fine, crosshatched lines, each line representing a tiny groove in the surface of the aluminum.

Figure 1B:
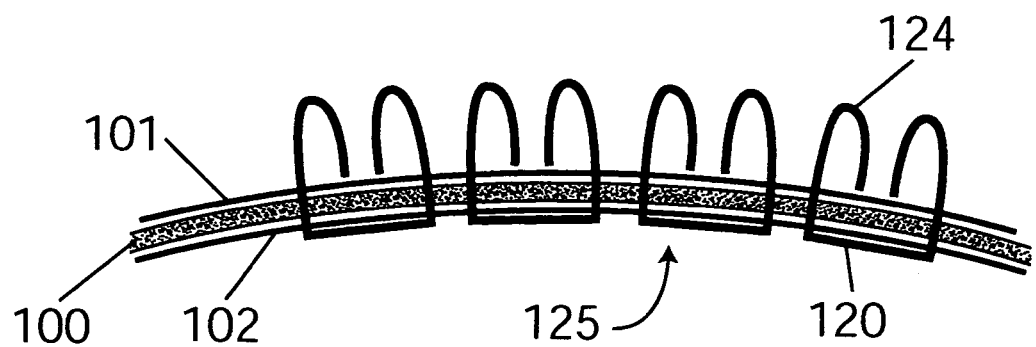
FIG. 1b is a close-up view of a section common to fan-free embodiments.

FIG. 1b shows a section view of reservoir 100 with four elements 120. Reservoir 100 can be made of any strong, flexible, preferably elastic, rapidly wicking and highly absorbent material such as nylon/spandex or cotton/spandex fabrics. In most embodiments, for the sake of the user's comfort, reservoir 100 is preferably less than one tenth of an inch thick.

Reservoir 100 can have a continuous outer reservoir barrier 101 on the outside-facing surface to prevent water from evaporating directly from the fabric into the air, rather than from the surfaces of elements 120, thereby conserving water and prolonging the cooling effect before rewetting. Alternatively, outer reservoir barrier 101 can be discontinuous, providing some protection from evaporation while still allowing the user to wet reservoir 100 directly.

Reservoir 100 can (and, in most cases for comfort should) also have an inner reservoir barrier 102 on skin-facing surface 125 to prevent moisture in reservoir 100 from wetting the user's skin. To insure a completely waterproof seal, inner reservoir barrier 102 can cover both primary fluid reservoir 100 the skin-facing portions of elements 120. However, this creates the problem that almost any waterproof barrier, no matter how thin, also tends to act as a thermal insulator, reducing the cooling effect. Experiments show that a comfortable, waterproof, elastic barrier can be made by filling inner reservoir barrier 102 with aluminum powder (or other thermally conductive material), thus greatly increasing its thermal conductivity.

If both the inner and outer surfaces of reservoir 100 have a continuous moisture barrier, special means must be provided for the user to wet reservoir 100. This can include wetting:
- From the edges
- Through elements 120
- Through fluid delivery means that penetrate at least one reservoir barrier
- By making at least portions of reservoir barriers 101 or 102 removable for easy wetting Expression #1

Operation of Fan-Free Embodiments

Figure 2A:
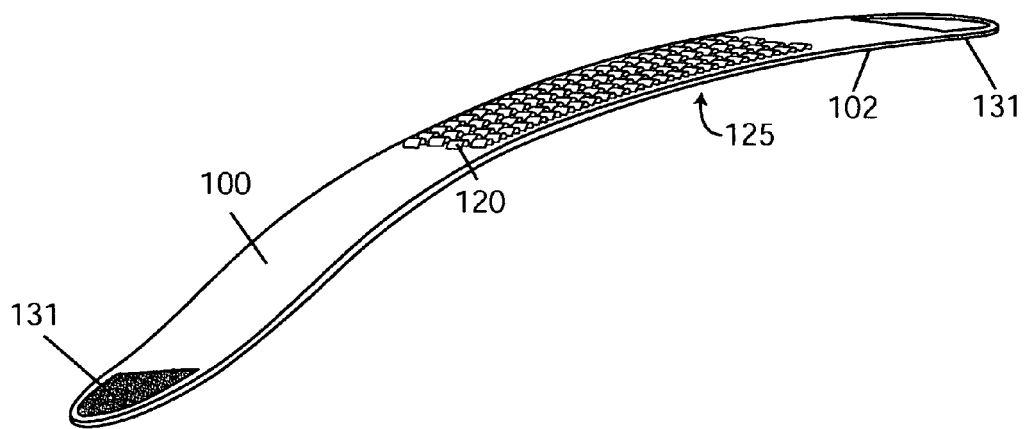
FIG. 2a shows a fan-free headband embodiment not being worn.

FIG. 2a shows a headband embodiment prior to being worn. A grid of elements 120 penetrate reservoir 100 as previously described, and inner reservoir barrier 102 (not seen in this view) protects the user's skin from being wet. Outer reservoir barrier 101 keeps water from evaporating directly into the surrounding air, forcing all of it to migrate onto surfaces 124 before evaporating. Hook-and-loop fasteners 131 at each end allow the user to secure the device to his or her forehead.

Figure 2B:
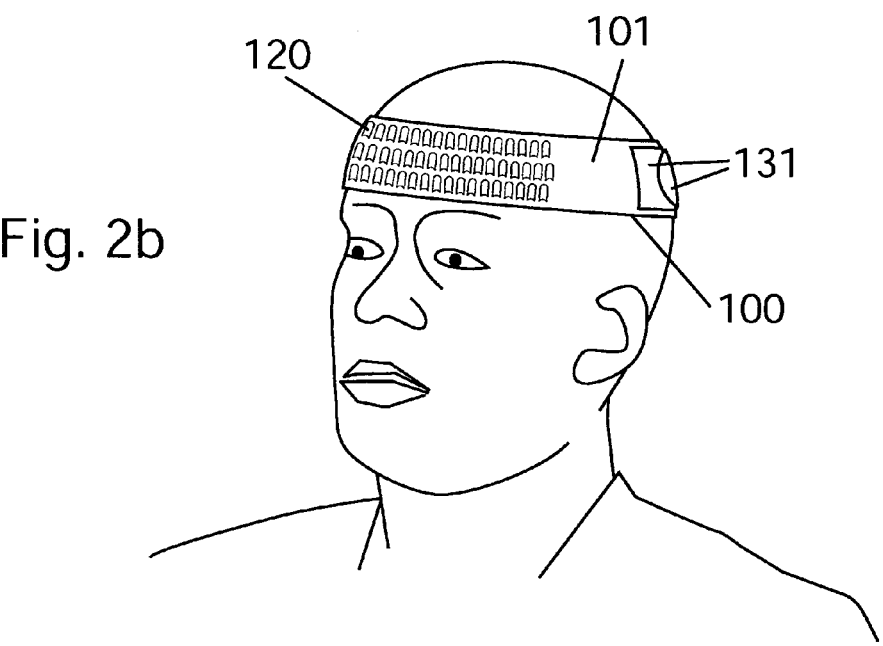
FIG. 2b shows the headband embodiment of FIG. 2a being worn by a user.

Different embodiments can provide different ways to soak reservoir 100, such as by immersing the device in a basin of fluid, by dousing it with a hose, or by squirting or spraying it with liquid from a container. In the embodiment shown in FIG. 2a, because reservoir 100 is sealed on skin-facing surface 125 and because outer barrier 101 blocks a users from spraying or squirting water on it, the user can simply immerse the device in a sink and the water will seep into reservoir 100 around the edges of slits 104 and by migrating through elements 120. The user then places skin-facing surface 125 against the forehead, and secures the opposing ends of the device to each other by means of a fastener such as hook-and-loop fasteners 131. Of course, a clip, belt, catch, clasp, hasp, snap, etc. can also be used. FIG. 2b shows a user wearing the device.

Once reservoir 100 is wet, fluid will migrate onto fluid-wicking surfaces 124 of elements 120 by capillary action. Because the fluid is spread in a very thin layer over a relatively large surface area, the surrounding air has easy access to the molecules of water, and readily absorbs it according to the air temperature and humidity. As the evaporating water is carried into the surrounding air, it carries with it heat that was in elements 120. As elements 120 cool, they absorb heat from the user's skin, thereby cooling the user.

Figure 2C:
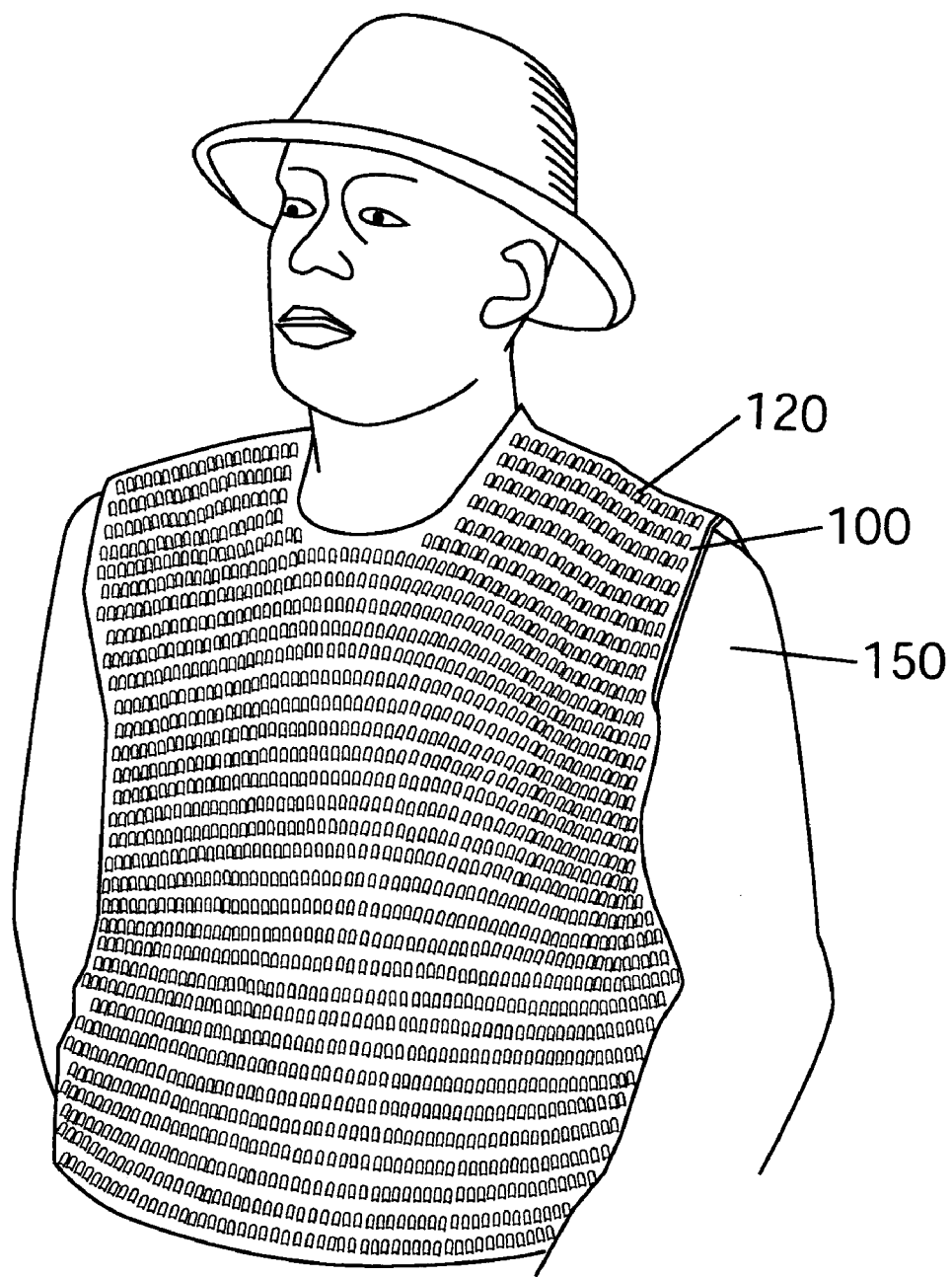
FIG. 2c shows a fan-free T-shirt embodiment for cooling a user's torso.

If the device was made elastic to fit a range of body sizes, it can simply be slipped on and adjusted for comfort. For example, FIG. 2c shows the device made as a T-shirt that is simply pulled on over the head. Elements 120 are preferably in solid contact with the user's skin to promote the transfer of heat from the skin through the device and into the air. To accommodate a wider range of sizes, the device can be made elastic and also provide an adjustable fastening system. For example, a head cooler can be made elastic, and it can also use hook-and-loop fasteners 131, allowing the user to adjust the tension of the device against the skin.

Expression #1

Fan-Free Clothing and Accessory Embodiments

The flexibility of the device allows it to be configured to comfortably cool almost any part of a human or animal body. FIGS. 2d-j show some of the many additional embodiments beyond those already described.

Figure 2D:
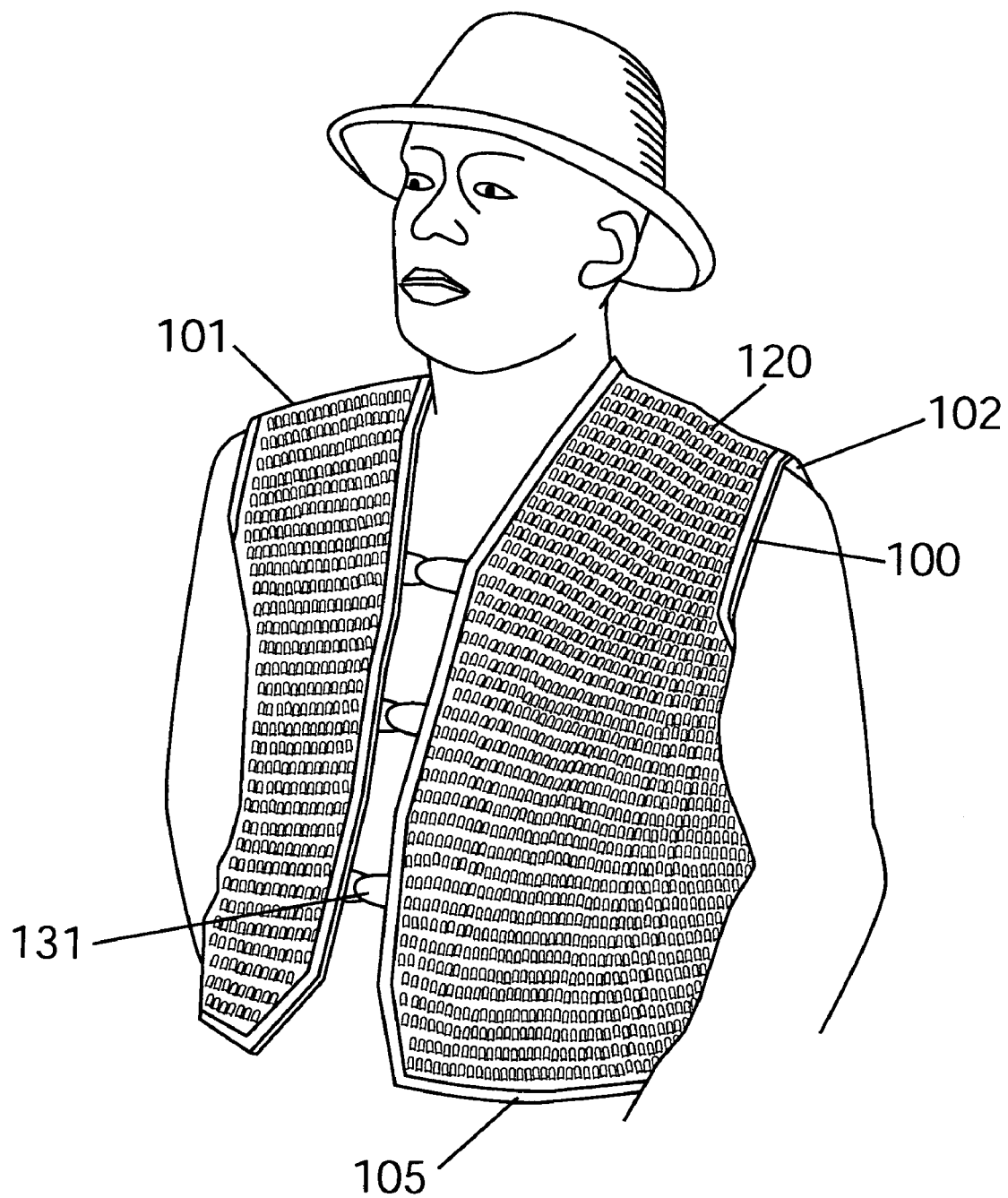
FIG. 2d shows a fan-free vest embodiment for cooling a user's torso.
Figure 2E:
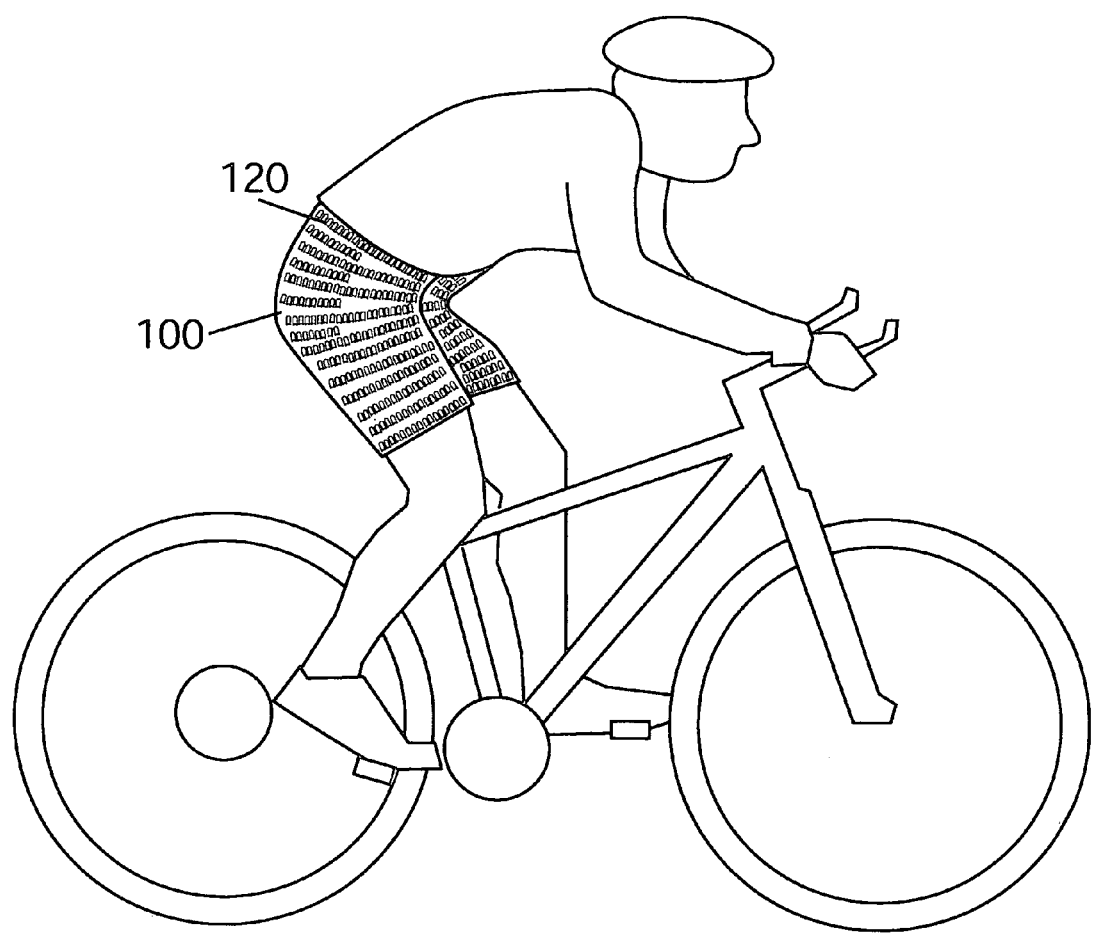
FIG. 2e shows a fan-free elastic shorts embodiment.
Figure 2F:
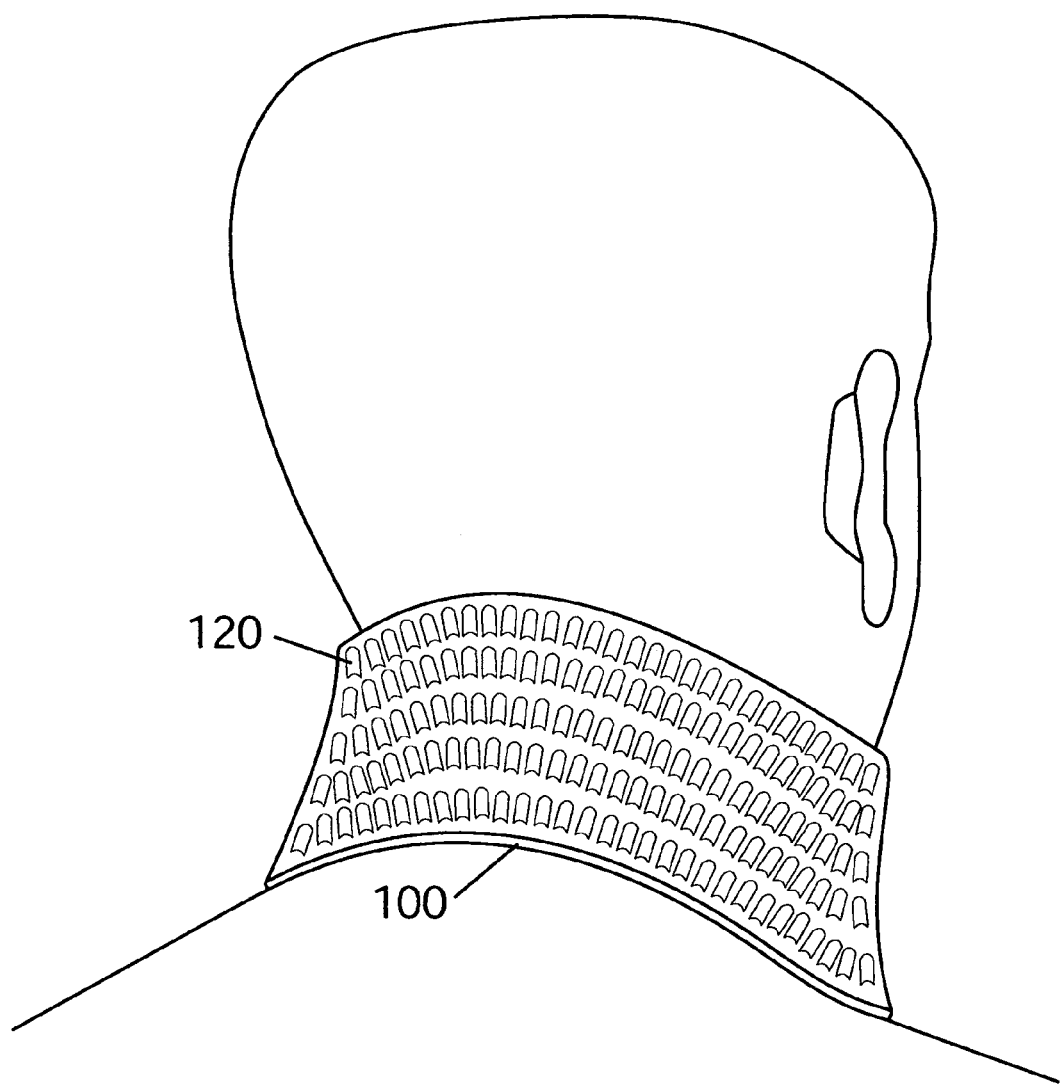
FIG. 2f shows a fan-free embodiment for cooling a user's neck.
Figure 2G:
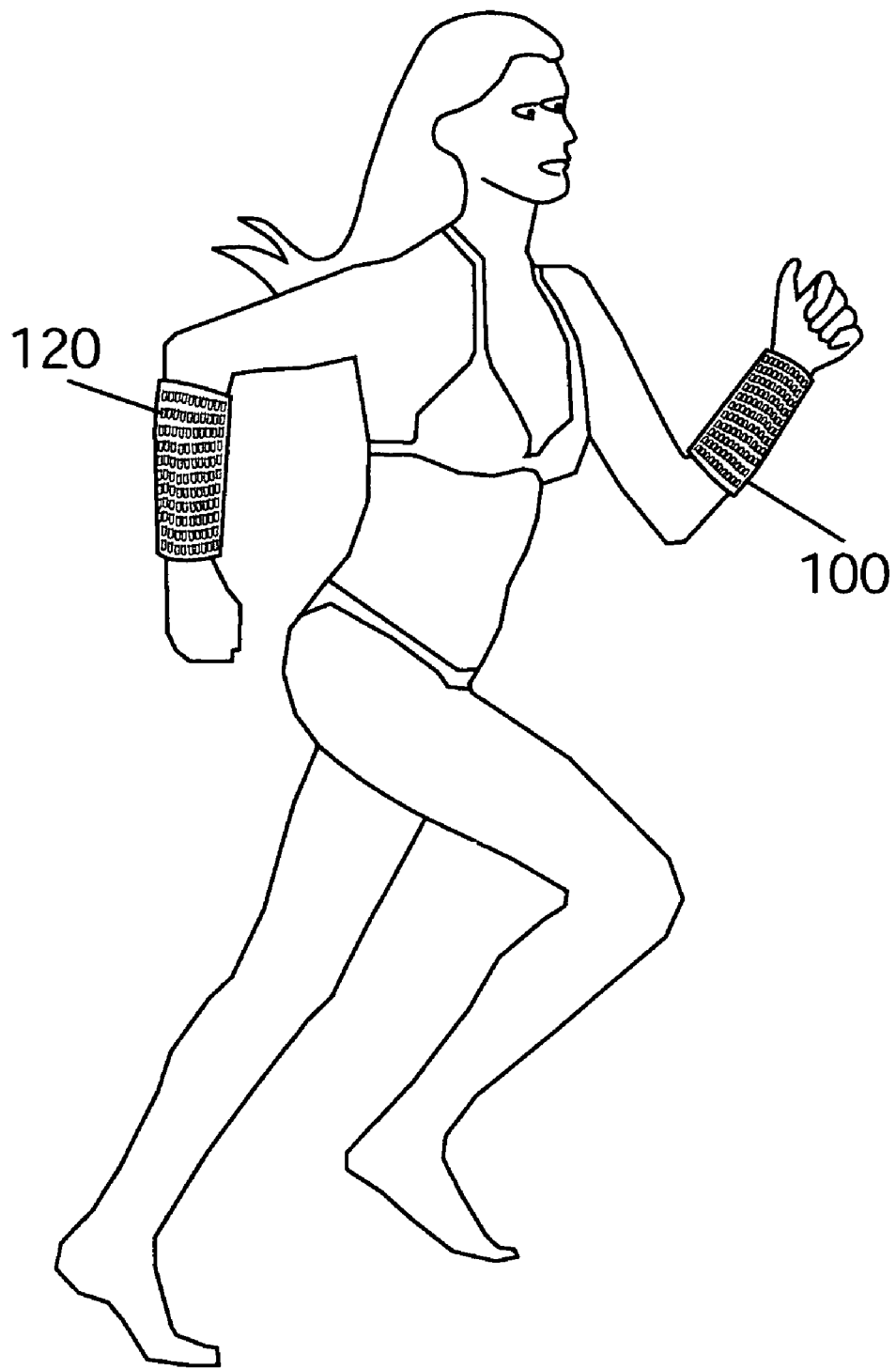
FIG. 2g shows a fan-free embodiment for cooling a user's forearms.
Figure 2H:
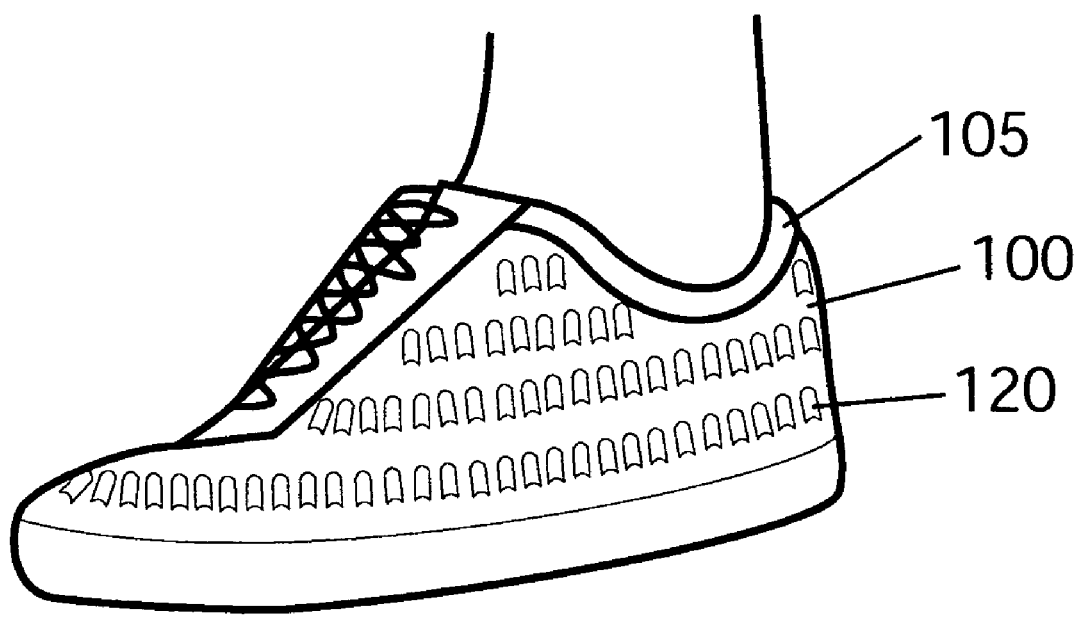
FIG. 2h shows a fan-free sneakers embodiment for cooling a user's feet.

FIG. 2d shows a user wearing a cooling vest embodiment. To prevent the user's clothing from being wet by contact with the edges of the device, device edges 105 can be sealed in a number of ways, including:

- By sewing or gluing a strip of waterproof material around the edges
- By dipping the edges in a waterproofing liquid, plastic, or sealer
- By rolling the edges into a seam that is sewn or heat sealed FIG. 2e shows a user wearing an elastic shorts embodiment. FIG. 2f shows a user wearing a neck cooler embodiment. FIG. 2g shows a user wearing embodiments designed to cool the forearms. FIG. 2h shows a footwear embodiment. All of these embodiments are essentially the same with a few changes in the materials used and the ways they are finished; they are simply shaped differently to fit different body parts.

Embodiments for human users that can be worn as clothing include long and short sleeved shirts or blouses, shorts, pants, jeans, jackets, vests, dresses, skirts, jumpsuits, robes, bathing suits, sleepwear, hosiery, athletic wear, uniforms, and costumes. In short, the device can be embodied as virtually any article of clothing. Accessory embodiments can include coolers for the head, neck, shoulders, chest, back, upper arms, lower arms, wrists, hands (gloves), upper legs, lower legs, and feet (boots, shoes, and sandals).

Figure 2I:
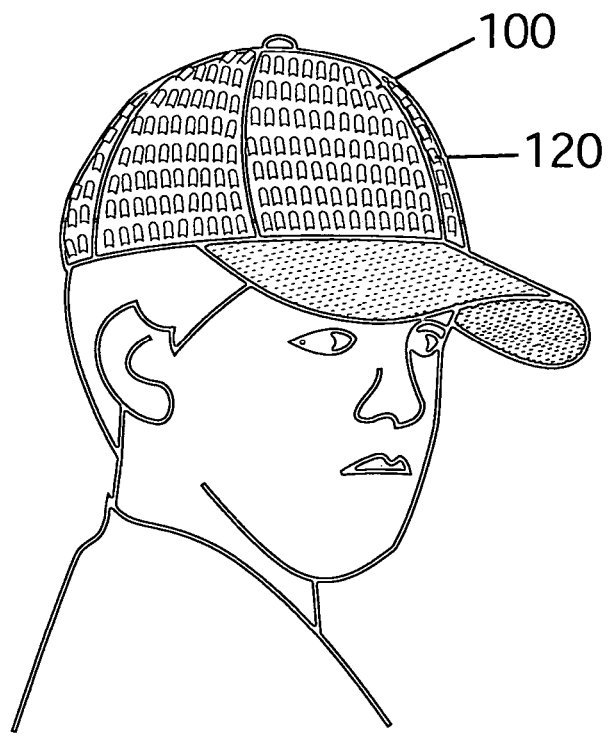
FIG. 2i shows a fan-free baseball cap embodiment for cooling a user's scalp.
Figure 2J:
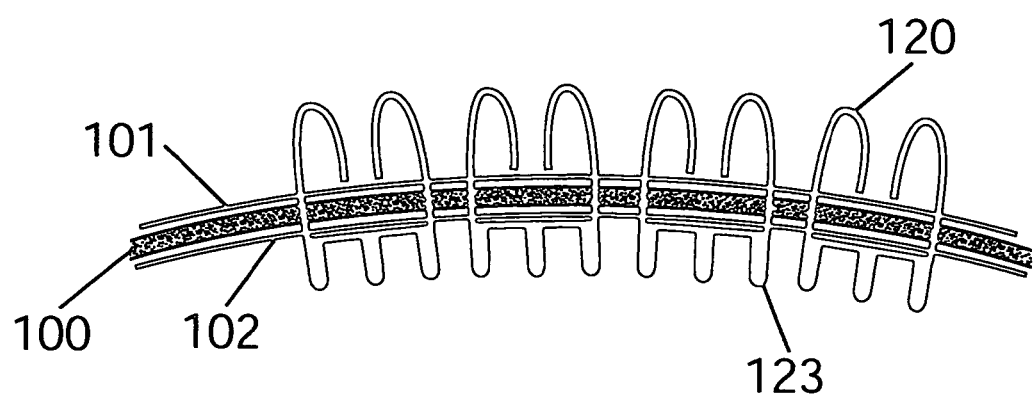
FIG. 2j shows a close-up of special element extensions for penetrating hair or fur.

Hats, caps, and hoods provide a particular challenge. The hair covering human heads makes it difficult to deliver cooling relief to the scalp. FIG. 2i shows a fan-free cooling cap that, like the other embodiments discussed, is essentially a flexible or elastic fabric studded with elements 120. FIG. 2j shows a close-up view of a section of the cap. By simply extending the bottom part of elements 120 into rod-like extensions, elements 120 will penetrate the user's hair (in the manner of a loosely-spaced plastic hairbrush) and touch the scalp. Extensions 123 are rod-like protrusions with rounded ends smooth enough to feel comfortable. They can be deformed, cast, or extruded as part of elements 120, or they can be separate pieces that are attached through any useful means (such as welding, soldering, brazing, gluing, or mechanically attaching) so long as they conduct heat from the scalp to elements 120.

A full-body jumpsuit embodiment can be created with many detachable parts. The collar can be detached; the forearm pieces, upper arm pieces, lower leg pieces, etc., according to the user's need in the moment. In extremely hot environments, the suit can even incorporate an elastic hood that detaches from the collar piece or can be pulled off the head.

Expression #1

Fan-Free Devices as Protective Clothing and Helmets

People often need to wear protective clothing or helmets that create extra discomfort in heat. Workers required to wear gear for protection from an array of dangers (including radiological, biological, physical, thermal, and chemical hazards) would all benefit from the ability to control their thermal comfort while remaining safe. Technicians and industrial workers (welders, sandblasters, coatings sprayers, etc), firefighters, rescue workers, chemical and biohazard remediation personnel, military and law enforcement people wearing body armor are among many who would benefit greatly from the ability to stay cool on the job. Workers wearing uniforms are also often made very uncomfortable in hot weather and conditions. And today, people all over the world are forced to wear long shirts and pants to protect themselves from increasingly harsh solar radiation.

In situations where mild or less predictable cooling is acceptable, or where the extra visual bulk of forced-air embodiments is unacceptable, fan-free embodiments of the device can be created to protect a user's body from hazards while also providing cooling. The primary key is the material used as outer reservoir barrier 101 (shown in FIG. 1b). Because the cooling effect is undiminished by the type or thickness of outer reservoir barrier 101, it can be made of any suitable material such as rubber for sandblasting, polyethylene for chemical resistance, etc. If outer reservoir barrier 101 needs to be thicker than about one hundred and fifty thousands of an inch, elements 120 may need to be made longer than usual and thicker than twenty-five thousandths of an inch to maintain sufficient heat transfer through the length of the fins.

If double protection is needed, inner reservoir barrier 102 can also be made of a protective material. If triple protection is needed, reservoir 100 can itself be composed of protective material, provided it is both flexible and absorbent as well as preferably elastic. The points of intersection between elements 120 and reservoir 100 must be carefully sealed to prevent hazardous materials, gasses, or radiation from leaking through to the user's skin. In this case, the two-part version of elements 120 discussed later may work better.

In the case of a chemical protection suit, reservoir barriers 101 and/or 102 can, for example, be latex, polyethylene, ethylene-vinyl alcohol, multi-layered film barrier composites, soft polypropylene laminated fabrics, aromatic polyamides, or any of the hundreds of different materials currently used to resist chemicals. If the device is used to protect against chemicals that can react with whatever material comprises elements 120, the surface of elements 120 can be treated for protection from such chemicals or elements 120 can be made of a material that will not react with the chemicals in question.

An embodiment providing physical protection for motorcyclists can use leather as outer reservoir barrier 101, thereby offering physical protection along with effective cooling power. An alternative fan-free motorcycle jacket can be created by combining a fan-free shirt embodiment to be worn against the skin with a leather jacket providing vents in the front and the rear. When a biker is on the road, wind will rush into the device through the front vents, evaporate water from the surfaces of elements 120, and exit through the rear vents.

I also anticipate fan-free helmet embodiments designed to make use of the air rushing past a bicyclist or motorcyclist when in motion. Air intake vents can be slits toward the front of the helmet, funneling the moving air directly to the tops of elements 120. Slits in the rear of the helmet will allow the rushing air to escape, thereby freeing the device of any need for fans or batteries.

Expression #1

Fan-Free Blankets, Shawls, and Wraps

Many people have the problem of living in climates so hot at night that it's difficult to sleep. Fans can cool a user, but it can be disturbing to have air moving across the body when trying to fall asleep. Many people are made uncomfortable by having to remove all covers in order to be cool enough, and tend to use at least a sheet, even if that makes them hotter. Air conditioners work well, but also create potentially annoying air movement and noise, and are expensive to run all night. A fan-free or forced-air embodiment in the form of a blanket or sheet would allow users to simultaneously feel cozy and stay cool, without having air moving against their skin, paying for air conditioning, or being irritated by the noise of a large fan or air conditioner.

Figure 2K:
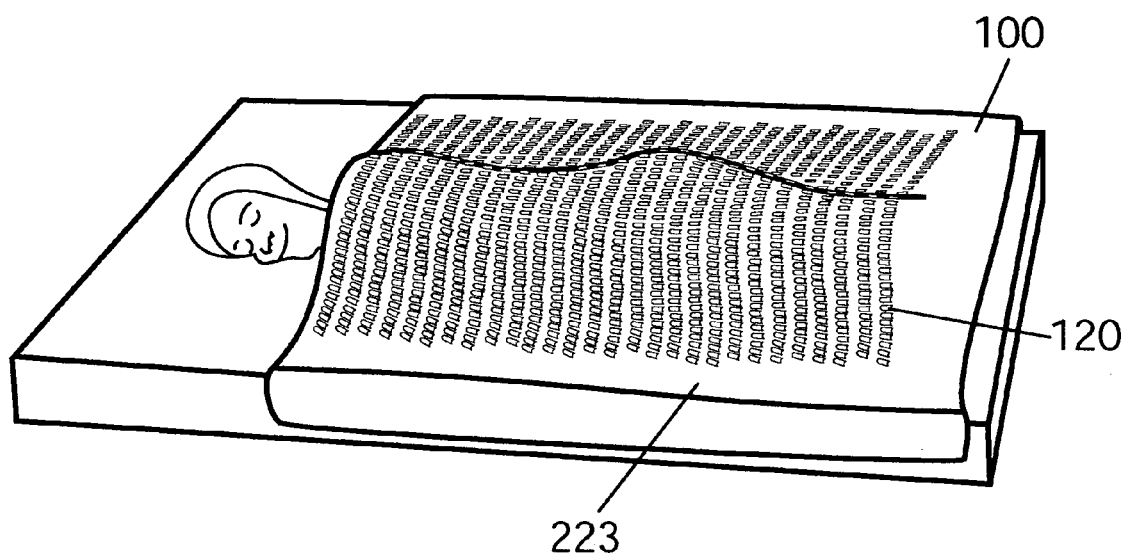
FIG. 2k shows a fan-free cooling blanket embodiment
Figure 2I:
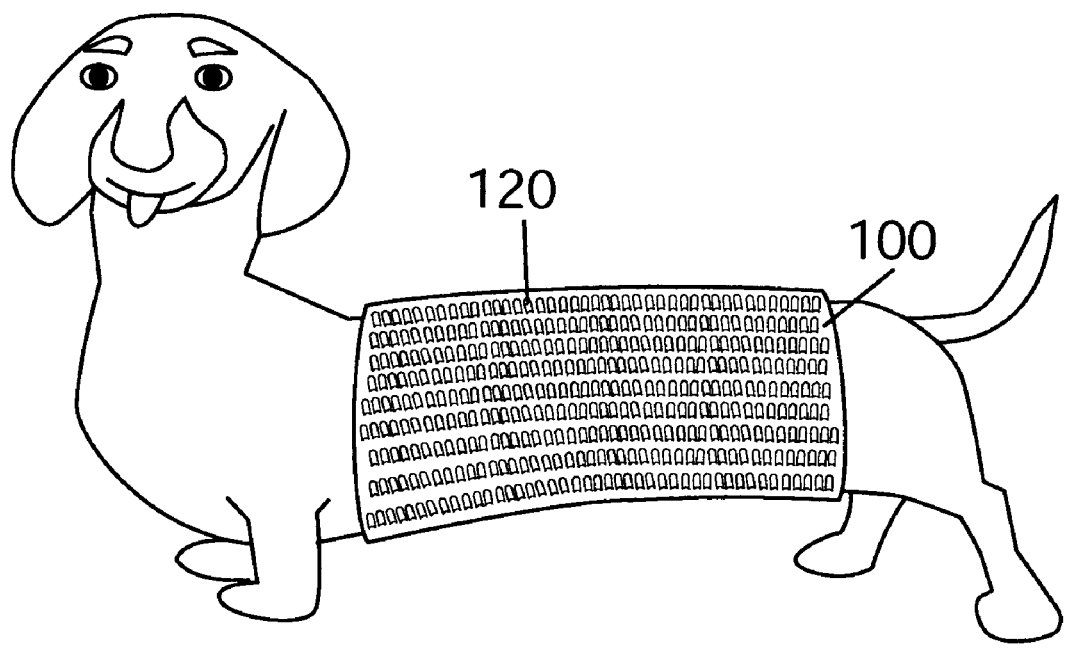

FIG. 2k shows a fan-free cooling blanket embodiment. As usual, there is a reservoir 100 in the form of a flexible, absorbent fabric, studded with a grid of elements 120. As previously described, the skin-facing surface of the blanket is coated with a flexible, waterproof, thermally conductive inner reservoir barrier 102, not shown in this view. Element-free zone 223 is provided because elements need only be closer to the center, where the user's body is likely to be. The user would simply pour a glass of water on the center of the blanket and get cozy. The water will rapidly migrate throughout reservoir 100, onto the fluid-wicking surfaces 124 of elements 120, and evaporate into the surrounding air, thereby cooling the user.

Expression #1

Fan-Free Embodiments for Dogs and Other Animals

Many dogs have been bred with long hair for colder environments, but are raised and cared for by owners who live in warm or hot environments. Additionally, pet owners often face the challenge of needing to leave a dog in a locked vehicle with the windows closed for security, but want to protect them from too much heat if the vehicle is parked in the sun. Other animals are often exposed to excessive temperatures, especially during heat waves, and their owners would like to keep them cool.

The main problem in cooling animals is that, as with the hair on human heads, their fur acts as a thermal insulator, preventing the evaporative cooling effect of water from fully reaching their skin. None of the evaporative cooling devices mentioned in the cited prior art would work for a fur-covered animal. Devices that spray water and/or blow air would have a negligible effect.

FIG. 2l shows an embodiment for cooling a dog. Except for its shape and a few other details, it provides essentially the same solution for dogs and animals as the baseball cap in FIG. 2i provided for humans. FIG. 2l shows the outside of the device as a fabric studded with elements 120. The inside of the device is exactly like the detail shown in FIG. 2j, with element extensions 123 protruding from the bottoms of elements 120, thereby penetrating through the animal's fur and delivering cooling relief directly to the animal's skin.

Expression #1

Using Fan-Free Devices for Both Cooling and Warming

Fan-free embodiments can be used for both cooling and warming, according to the needs of the user. On a hot day, a user can wear one set of clothes that will maintain thermal comfort day and night, indoors and out. A user can put on a fan-free long-sleeved shirt embodiment and a fan-free jeans embodiment and head out into the sun. Because the plurality of cooling elements creates a huge surface area from which moisture can evaporate (thereby removing more heat than is removed through perspiration), the user will actually be cooler under the heavier cooling clothing than if he or she had ventured out with no clothing at all.

If a user steps into an air-conditioned building, he or she need only throw an extremely light outer covering over the shirt and/or jeans, and suddenly not only can the water no longer evaporate, but the thermal insulation provided by reservoir 100, outer reservoir barrier 101, inner reservoir barrier 102, air space 165, and the thin outer shell will act as a jacket, quickly warming the user. An outer layer to be thrown over the device can be sold as an integral part of the system and can also be packed into a tiny bag or be kept in a pouch or pocket that is part of the device. Whether the user throws on an outer shell that is designed to be used with the device, or uses an existing article of clothing, they should block all potential air exits by buttoning the wrists, tucking in a shirt or blouse, etc. to prevent air from circulating around elements 120, thereby reversing the desired warming effect.

Expression #1

Variations in Water Storage and Delivery Systems

There are many ways to store the water (or other cooling fluid), distribute it, and wet reservoir 100 as well as elements 120. In the embodiments discussed so far, water was stored in primary reservoir 100, which automatically distributed the moisture by capillary action to elements 120. To wet reservoir 100 in the devices so far described, the user can douse the device in a sink or other body of water, spray it with a hose, or wet it by sparing with a stream or spray of liquid from a bottle.

However, such wetting methods have serious drawbacks, such as that the user might:

Not wish to get themselves wet in order to wet the device,
Not wish to remove the device in order to wet it,
Not wish or have the option to jump in a shower, tub, lake or other body of water to wet the device,
Not have or wish to use a spray bottle to wet the device,
Have difficulty wetting parts of the device that can't been seen or reached,
Be unable to determine which parts of the device need water,
Put too much water on part of the device, resulting in it dripping off and potentially wetting their other clothes or shoes, or spilling on the floor.

Figure 3A:
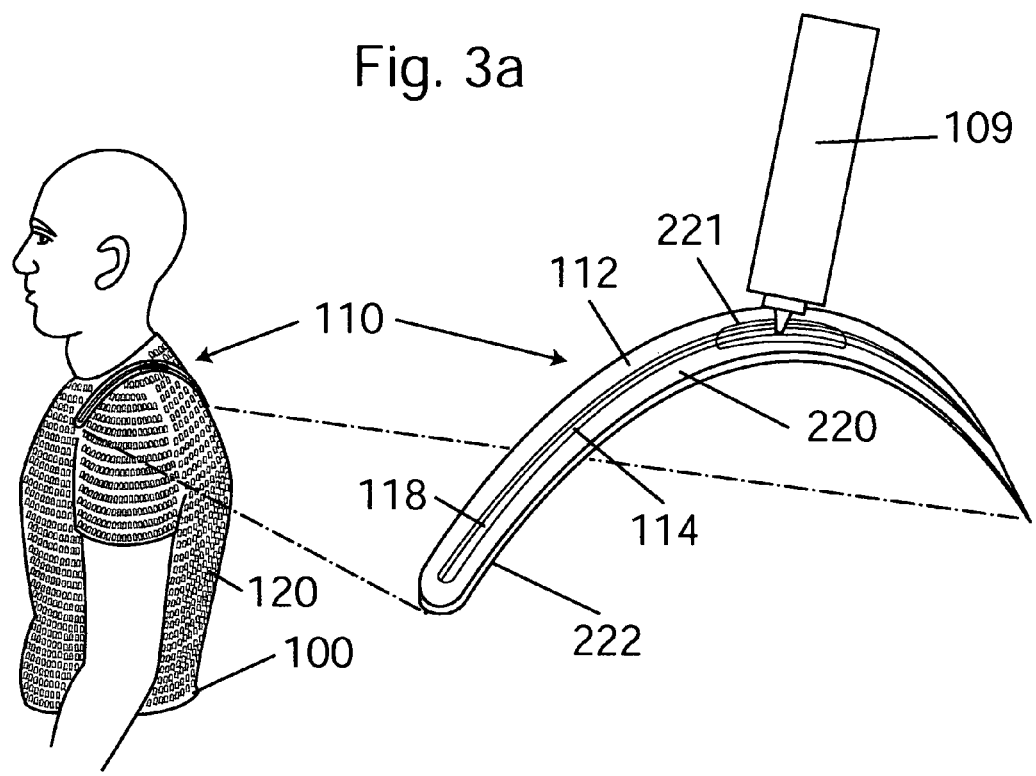
FIG. 3a shows one way of creating a reservoir for storing additional fluid.

There are several ways to resolve these problems. FIG. 3a shows that one or more additional reservoirs 110 can be provided around the device, which the user can fill or soak from an external reservoir 109 (such as a bottle) without overfilling or causing excess water to spill on the user or the floor. The illustration shows a user wearing an elastic T-shirt embodiment with long, thin additional reservoirs 110 placed on the shoulders. Embodiments using capillary action to distribute water should place at least one additional reservoir 110 at or near the highest point on the device. This is because, although water will migrate uphill through absorbent materials, due to the effects of gravity it does so more slowly than it migrates downhill.

Running through the length of additional reservoir 110 is a long notch 114. Attached to the entire bottom of additional reservoir 110 is a piece of wicking material 118 serving as reservoir bottom 222, such as a piece of tightly woven cloth or a thin piece of porous plastic, which provides a way for water to be channeled to both ends, rather than splash directly onto elements 120 and/or reservoir 100. Material 118 also creates a wicking interface between sponge 112 and the tops of element 120. Attached to the entire top of additional reservoir 110 is a piece of waterproof material (in this case, a clear flexible plastic) functioning as reservoir cover 220. In the center of reservoir cover 220 is a long oval reservoir opening 221. A user can take an external reservoir 109 such as a water bottle with a pointed top, insert it into the slot exposed by reservoir opening 221, urge it toward the front end of reservoir opening 221, and squeeze. Water will flow from external reservoir 109 into notch 114, and as it runs downhill it will be absorbed by sponge 112 on each side. The user can then slide the tip of the water bottle back until it hits the back end of reservoir opening 221, and squeeze again to wet the sponge in the back part of additional reservoir 110.

Figure 3B:
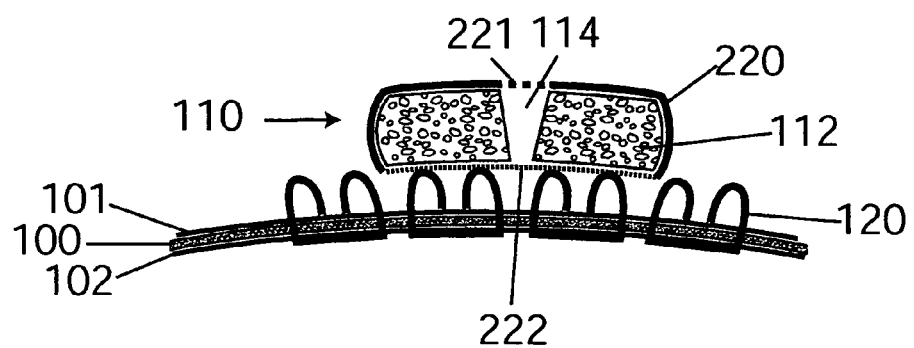
FIG. 3b is an edge view showing the additional fluid reservoir of FIG. 3a on top of elements.

FIG. 3b shows a section view in which reservoir 110 sits on top of elements 120. Alternatively, elements 120 can be kept outside the area where reservoir 110 is located, allowing reservoir 110 to make direct contact with reservoir 100.

Figure 3C:
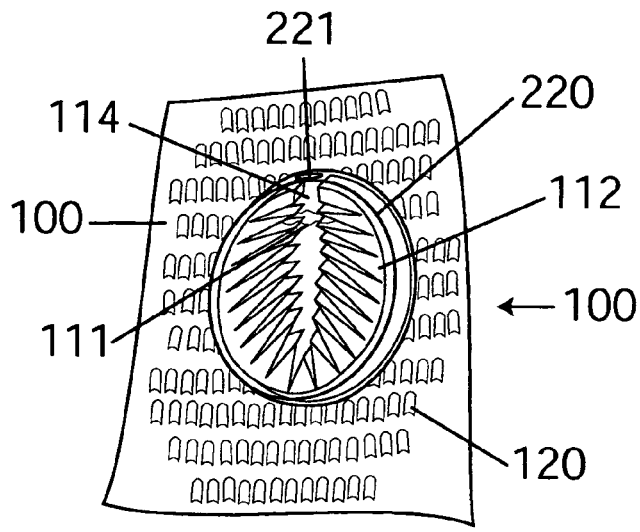
FIG. 3c is a front view of a soft, clear, sponge-filled additional fluid reservoir.
Figure 3D:
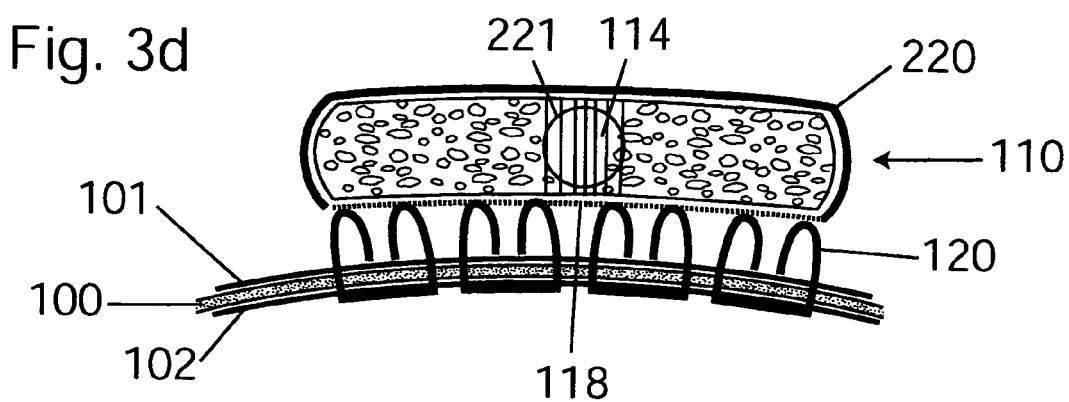
FIG. 3d is a top view of additional fluid reservoir sitting on top of elements.
Figure 3E:
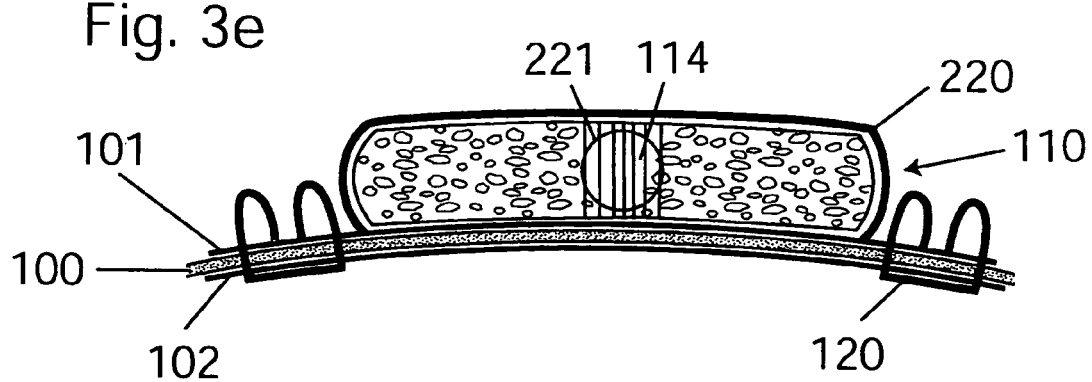
FIG. 3e is a top view of additional fluid reservoir in direct contact with primary reservoir.
Figure 3F:
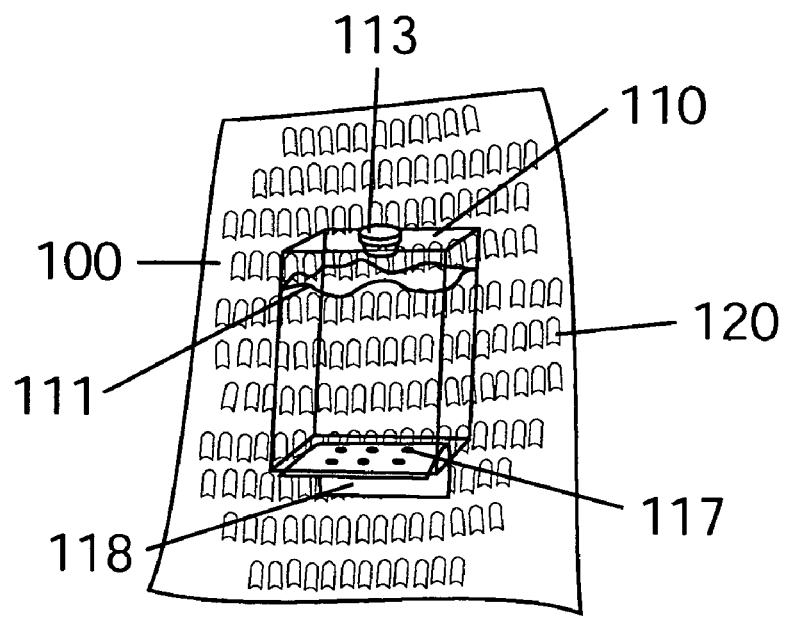
FIG. 3f shows additional fluid reservoir as a hard, clear box.

As long as they absorb water, additional reservoir(s) 110 can be rigid or soft, and can be filled with an absorbent material such as a sponge 112, or not. FIG. 3c shows additional reservoir 110 with reservoir cover 220 as a soft clear vinyl case over sponge 112. Reservoir opening 221 allows a user to pour water directly into notch 114 in sponge 112. Notch 114 in sponge 112 can be open from the front to the back of additional reservoir 110, allowing the user to see when the reservoir is filled before it overflows. A user can take an external reservoir 109 such as a water bottle, insert its tip into reservoir opening 221, and squeeze. By peering through clear reservoir cover 220, a user can see water line 111 as it fills additional reservoir 110. FIG. 3d shows a top view of reservoir 110 sitting on top of elements 120. FIG. 3e shows reservoir 110 resting directly on reservoir 100, with no need for wicking material 118 as an interface FIG. 3f shows additional reservoir 110 as a stiff clear plastic box not filled with a sponge. A user can remove reservoir cap 113 and squeeze water into reservoir 110 from a bottle. Holes 117 in reservoir bottom 222 allow water to drip onto wicking material 118, which transfers the moisture by capillary action to the tops of elements 120, directly to reservoir 100, or both. Of course, holes 117 can be in the back of additional reservoir 110, with wicking material 118 inserted as a wicking interface between the back of the reservoir 110 and the tops of elements 120. Alternatively, reservoir 110 can be shaped so that holes 117 are in direct contact with reservoir 100, so that no other wicking material 118 is needed.

Figure 3G:
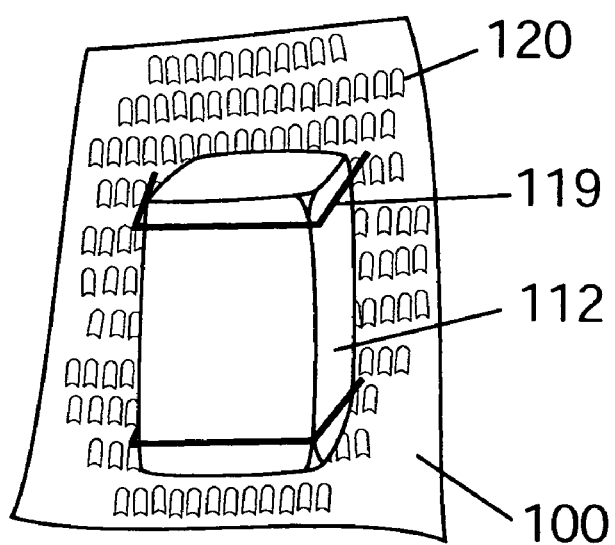
FIG. 3g shows additional fluid reservoir as a sponge.

Additional reservoir 110 can be made detachable from the device so instead of squirting water into it, it can instead be submerged in a body of water or placed under a spigot. In another approach, if reservoir 110 has a sponge 112 and a cover 220, the user can open a door, pull out sponge 112, soak it in water, place it back inside reservoir cover 220, and close the door. FIG. 3g shows that sponge 112 need not be enclosed in a separate cover, and can be detachably secured by a sponge holder 119 such as wires, straps, or plastic shapes. In this case, sponge 112 can be protected by a watertight barrier on the outside-facing surfaces to prevent water from evaporating directly from sponge 112 into the surrounding air. As long as the device-touching surface of sponge 112 is exposed, water can migrate from sponge 112 directly onto the tops of elements 120. If elements were not placed in the sponge area, water can migrate directly from sponge 112 to reservoir 100.

Expression #1

Water Storage and Delivery Design Considerations

The fewer the number of additional reservoirs 110 provided for the user to fill, the more convenient it will be for the user, yet the more important it will be for either reservoir 100 or any fluid delivery means to promote water to wick across the entire length of the device. Ideally, each device would have just one or two additional reservoirs 110. Having just one or two reservoirs 110 also provides a minimum number of points from which the water level can be monitored. In a low-tech water monitoring approach, the user can simply look through clear reservoir cover 220 and see if more water is needed. To make dryness more obvious, sponge 112 can be impregnated with cobalt chloride or any chemical that turns a different color when wet vs. when dry. In a high-tech approach, the system can electronically detect when the system is low on water (such as by measuring electrical resistance between two points on the device) and can activate an alarm, blinking light, voice notification, etc., alerting the user to add water.

The device can incorporate means to manually or automatically spray water stored in additional reservoirs 110 onto elements 120, but any such approach would likely be far more complex and far less practical than the various capillary distribution means already discussed. If automated means are used, it can include commonly available means to determine when extra water is needed.

Assuming capillary or wicking action is used, water will be drawn automatically from the reservoir to drier parts of the device as needed. Alternatively, instead of being essentially sponges, additional reservoir(s) 110 can be watertight bottles from which fluid can drip or flow by gravity through tubes or channels that connect additional reservoir(s) 110 to various parts of the device. If the system depends on gravity to deliver the water (a more complicated and less efficient solution), the user will need to manually turn the water delivery system on and off, or an automatic system will be needed that can sense the dryness of an area and activate valves to start and stop water flow. This configuration would also require additional reservoirs (110) to have watertight lids, an extra hassle for the user to deal with.

Expression #1

Variations on Elements

FIG. 4a shows a variation on the shape of elements 120, in this case to add more surface area. Elements 120 can have any shape as long as they wick fluid and conduct heat.

In FIG. 4b, elements 120 are composed of two parts. Bottom element part 121 is designed to be in contact with the user's skin, and to interlock with top element part 122 through a hole it punches in reservoir 100 and reservoir barriers 101 and 102. Top element part 122 is designed to snugly interlock with bottom element part 121, to be fluid wicking, and to conduct heat. Top 122 and bottom 121 are designed to permanently mate in the manner of a snap-together fitting. It is important that both parts mate together tightly so heat conducts well between the two parts. This approach allows elements 120 to be secured to reservoir 100 without using glue, while sealing the intersection and preventing moisture in reservoir 100 from wetting the user's skin.

FIG. 4c is essentially the same, but has a more rounded top part 122 to make the outside of the device smoother to the touch. FIG. 4d shows how top part 122 can provide extra surface area for evaporation. Bottom part 121 can also have extensions 123 when elements 120 are used to cool skin through hair or fur.

A permanent two-part element system can be created as a do-it-yourself kit, allowing consumers to turn existing garments or accessories into cooling devices. FIG. 4e depicts a special snap tool 190 that functions like a pair of pliers. Tool 190 has lever arms 191, a pivot point 192, and jaws 193. A user would place top element part 122 into holder for element top 194, bottom element part 121 into holder for element bottom 195, place existing clothing article 194 between open jaws 193, and squeeze lever arms 191 together until the two element parts penetrate the article and snap together.

FIGS. 4f-h show three different ways to make a removable two-part element system that would allow users to manually insert elements 120 without a special tool. All three are based around a central pin-like stud that will penetrate through the fabric of an article of clothing without tearing it. FIG. 4f shows an embodiment that functions in the manner of a snap. Bottom element part 121 has a pointed protrusion with a male snap shape 201. Top element part 122 has a female snap shape 202 to receive male snap shape 201. A user simply presses bottom element part 121 through the article of clothing, then presses top element part 122 down into bottom element part 121 until the two parts snap together. To remove them, the user pulls the two parts away from each other.

FIG. 4g show a system in which the sharp protrusion from bottom element part 121 is a male threaded stud 203, and top element part 122 has a female threaded socket 204 to receive it. The user simply presses bottom element part 121 through the article of clothing, then threads top element part 122 onto it.

FIG. 4h shows bottom element part 121 as a simple pointed stud with a slightly protruding ridge 208 that keeps top element part 122 from being easily pulled off bottom element part 121. Top element part 122 is much like a binder clip; it has two fluid-wicking fins 205, a "C" spring 206, and clip jaws 207. Fluid-wicking fins 205 must either be stuff enough to withstand being squeezed together many times by the user, or must be framed around the edges with a very stiff material. "C" spring 206 functions to hold top element part 122 to bottom element part 121. Clip jaws 207 are curved to make solid thermally conducting contact with bottom element part 121. The user simply presses bottom element part 121 through the article of clothing, then clips top element part 122 onto it.

In all three approaches, top element part 122 and bottom element part 121 must be created to mate closely to maintain maximum thermal conductivity between them. Top element part 122 must have wicking surfaces that will make a wicking contact with clothing article 164 when installed. Once the user has installed a plurality of elements into the article of clothing, he or she will put the article on and wet it. Water from the clothing will wick onto the fluid-wicking surfaces of top element parts 122 and evaporate, cooling the user.

Expression #1

Corrugated and Deformed Elements

Neither top element part 122, nor bottom element part 121, nor a single-piece element 120 can be made too large before it starts detracting from the flexibility and comfort of the device. However, if elements 120 are corrugated, they will themselves become flexible and can therefore be made much larger.

FIG. 4i shows how by taking strips of aluminum, making capillary micro-grooves in the surface (not seen in this edge view), and corrugating them in two dimensions (like the inside layer of corrugated cardboard), elements 120 can cover larger areas of the body while remaining flexible. The flexibility, however, is limited to one dimension, therefore any device making use of such corrugated strips will need to limit the width of each strip both for the user's comfort as well as for the sake of maintaining maximum contact between skin-facing surface 125 of the device and user's skin 150.

FIG. 4j shows a cooling vest made of such corrugated, fluid-wicking aluminum strips 126. In this configuration, the fluid storage and wicking functions performed by primary fluid reservoir 100 in previous embodiments are now assumed by the flexibility and fluid-wicking ability of 2-D corrugated element strips 126 themselves. Because little fluid can be stored in the capillary micro-grooves of elements 120, additional fluid reservoirs 110 (absorbent fabric or fluid-wicking foamy material) are provided. By placing them at the edges of the device, additional fluid reservoirs 110 double as a way to finish the sharp aluminum edges of strips 126 with a soft material that is comfortable to the skin.

It is desirable to keep the overall design elastic in order to maintain skin-facing surfaces 125 of elements 126 in contact with user's skin 150. To accomplish this, 2-D corrugated element strips 126 are connected via elastic connectors 115, preferably absorbent elastic fabrics. Fluid-wicking surfaces 124 face the outside, and skin-facing surfaces 125 are placed against the user's skin. When a user wets additional fluid reservoirs 110, water quickly spreads by capillary action onto the surface of 2-D corrugated element strips 126 and evaporates directly into the surrounding air. As with the previously described embodiments, the reason this improves on natural perspiration is because the corrugations in elements 120 create a surface area greater than the user's skin, thereby making much more water available at the surface for evaporation, which in turn increases the heat pump effect.

As previously mentioned, the disadvantage of 2-D corrugated element strips 126 is that they are not flexible in three dimensions. FIG. 4k shows how by taking thin sheets of surface-wicking aluminum (or other thermally conductive material) and deforming them into an egg-crate pattern, the elements become flexible in three dimensions. Fluid-wicking surface 124 faces the outside of the device, and skin-facing surface 125 is placed against user's skin 150.

FIG. 4l shows how, as in FIG. 10b with 2-D corrugated element strips 126, the same can be done with even larger pieces of 3-D corrugated elements 127 because they are more flexible and will therefore more easily maintain contact with the shape of the user's skin.

FIG. 4m shows how a cooling vest can be made from a single sheet of 3-D corrugated, fluid-wicking, thermally conductive material. Once the main body of the vest is formed, a manufacturer need only add additional fluid reservoirs 110 and hook-and-loop fasteners 131. One or more elastic belts 116 can also be provided to maintain contact between the device and the user's skin.

In the approaches described using corrugated materials, only the outside-facing surface of the device is treated or created to promote the wicking of a fluid. In another variation, skin-facing surface 125 of the device can also be created or treated to promote the wicking of water, with means to allow water to migrate from one surface to the other. A simple way to accomplish this is to make the device of a thin piece of aluminum with crosshatched grooves that penetrate more than 50% of the thickness on both sides. By making the grooves horizontally on one side, and vertically on the other, small gaps will be formed where the grooves intersect in the center of the thickness, allowing water to migrate from on side to the other. This configuration permits the user's own perspiration to add to the moisture being evaporated on the outside surface of the device. The drawback is that water added to the outside surface will be wicked onto the user's skin, creating potentially uncomfortable sensations.

The benefit of using a corrugated or deformed thermally conductive material created or treated to wick water is that it is extremely inexpensive to produce. The drawback is that it is far less flexible than the approach of interconnecting smaller elements 120 with a flexible material (such as a spandex fabric) as previously described, and is therefore less comfortable for the user.

In systems using both the 2-D and the 3-D corrugation embodiments just described, the more peaks and valleys per inch, and the taller the peaks and valleys, the greater the surface area and therefore the greater the cooling effect. A limit will be found, however, whereby the corrugations are so tight that air cannot move efficiently between the walls, and the evaporation rate will reach a practical maximum. In either approach, holes can be cut or punched in the aluminum sheet either before or after any of the other processes, to allow the user's skin to "breathe".

Expression #1

Variations on Means to Create Flexibility

In the previously described embodiments, the system derived its flexibility from the fact that elements 120 were joined by reservoir 100, which is at least flexible and preferably elastic. A variation just described provides flexibility by making corrugations or deformations in elements 120. FIG. 4n shows a perspective view of another variation on means to create device flexibility. Elements 120 are similar to the staple-shaped pieces described previously, but have four ends instead of two, and all are bent in and down toward the center as before. This allows them to be connected together in a grid pattern using non-wicking elastic connectors 225, such as rubber bands, springs, vinyl, etc., giving groups of elements 120 flexibility as a whole. FIG. 4o shows a top view of a group of elements 120 connected together.

The limitation of this configuration is that, without reservoir 100 or some other means to convey water between the elements, there is no obvious way to wet elements 120 and keep them moist. As previously mentioned, the device can incorporate means to manually or automatically spray water on elements 120, but any such approach is far more complex and tedious than by supplying water as previously described through a flexible reservoir such as an elastic fabric. Additional reservoirs can be suspended in the blank squares between elements 120, but that is almost the same as returning to embodiment #1, with elements 120 being supported by reservoir 100.

FIG. 4p shows a method that provides flexibility while also storing and distributing water and letting the user's skin breathe. Elements 120 penetrate the edges of elastic wicking fabric 115 (or other elastic wicking material), which stores water and wets both the inside and outside surfaces of elements 120. The square spaces between fabric 115 and elements 120 give the user's skin access to the surrounding air. This approach is essentially the same as was described in Expression #1 embodiments if holes had also been punched through reservoir 100.

FIG. 4g shows another variation in which elastic connectors 125 can be any material that is both fluid-wicking and flexible (preferably elastic), such as foam, elastic fabric, porous rubber, or porous elastomeric plastics. The resulting device will have air spaces that allow the user's skin access to the surrounding air so it can breathe. In this approach, water will be forced to migrate from one element to the next through elastic connectors 125.

Expression #1

Alternative Methods

Elements 120 preferably penetrate reservoir 100 and are secured to it by any effective means, including glue, or by virtue of the shape of elements 120 gripping or interlocking with reservoir 100 as discussed above. However, elements 120 do not need to penetrate reservoir 100; they can be attached to the edges of holes punched in reservoir 100. In either case, contact between elements 120 and reservoir 100 must allow fluid from reservoir 100 to migrate directly onto the surface of elements 120 by capillary action.

Elements 120 can also be made of a foamed thermally conductive material (such as foamed aluminum), which would serve two purposes: 1) to wick fluid up the elements for evaporation, and 2) to transfer heat from the skin to the evaporating fluid. However, the foamed aluminum available today is either far too expensive or not porous enough to wick water. In any case, it is anticipated that foamed aluminum or copper would not perform the thermal conductivity function as well as solid aluminum or copper with a micro-grooved surface.

Treatments to promote water to wick across the surface of elements 120 include but are not limited to:
1. Coating with powder, fibers, foam, or other water-absorbent material.
2. Printing a pattern of dots on the surface, thereby creating spaces between the dots for the water to wick by capillary action.
3. Powder-coating with a granular material, thereby creating spaces for the water to wick between the granules by capillary action.
4. Creating tiny parallel, linear grooves in the surface.
5. Creating tiny parallel or non-parallel cross-hatched or crisscrossed grooves in the surface Option 1 is inefficient because in general the coating itself acts as a thermal insulator, allowing water to evaporate, but reducing the heat transfer effect. Option 2 is technically difficult to produce and is not likely to be useful because anything printable on the surface (even aluminum powder) would need to include binders, which are at least mildly thermally insulating. For option 3, one of many effective capillary powder coatings can be made by adhering 100 mesh silicon carbide grit (commonly used for sandblast etching) to the surface of the aluminum elements using a urethane-based glue. Option 4 is not as effective as option 5 because it provides less surface area from which water can evaporate.

Option 5, described earlier as the preferred method, is by far the most effective because it does not insert any thermally insulating substances (such as glues, inks, powders, or granules) between the thermally conductive elements and the air. In addition, the cross-hatched or crisscrossed groove pattern provides for maximum water to migrate onto the surface for evaporation.

Micro-deformation using finning discs was earlier described as the preferred method of creating surface grooves. Such grooves can alternatively be formed by means of engraving, micro-machining, laser cutting, wire EDM (electrical discharge machining), and other methods. Grooves or channels can also be created by composing the elements of innumerable layers of extremely thin material, such as alternating widths of thin aluminum. When the layers are fused or adhered, the narrower layers form the bottoms of the capillary channels, while the wider layers form the walls of the channels. Such a process, however, is not likely to be cost effective.

An alternative way to prevent water from leaking onto the user's skin is to provide fluid-wicking surfaces on elements 120 only on the outside-facing areas of reservoir 100, but not continuing through to skin-facing surface 125. This approach, however, is not as waterproof as that mentioned just above. It would also be difficult to manufacture elements 120 using finning discs such that the cross-hatched grooves stop short of the skin-touching areas.

Expression #1

Design Considerations

The combination of reservoir 100 plus any additional reservoir barriers 101 and/or 102 must be strong enough to withstand the stresses of normal use when worn by a user. To help maintain tensile strength, each row of elements 120 can be offset so that slits 104 in reservoir 100 don't line up, since aligning them would effectively create an easy-to-tear perforated line. Other approaches can be employed to strengthen the device, such as by reinforcing reservoir 100 with a strong, flexible material at various points within and/or around the edges of the device. If such material also had wicking properties, it can double as an additional reservoir 110.

Problems can be created if elements 120 are placed in areas of the device that might come in contact with objects, such as the back of a chair or car seat. Solutions include:

Not placing elements 120 in such areas.

Insuring that elements 120 to be used in such areas have shapes that will neither cause damage to external objects nor discomfort when pressed against the user's skin.

Covering elements 120 in such areas with a material stiff enough to distribute the pressure of contact over a large area of elements 120.

Also, to prevent water in the device from wicking onto external objects, such as a car seat, or a fabric chair, pants bottoms, shirt backs, or vest backs can be isolated from the rest of the device.

If the stiff material for distributing weight were continuous (as in a thin sheet of plastic), it would have the effect of preventing the surrounding air from moving freely around elements 120, which would mediate the cooling effect. Using a fan to move the air in such areas would turn that area of the device into a forced-air embodiment as described next. If the stiff material for distributing weight were discontinuous (such as with a stiff plastic mesh), it can allow air to continue to circulate around elements 120 without the need for a fan.

Expression #2

Description of Integrated Forced Air Embodiments

The above-described fan-free embodiments are ideal for use in situations where:

The user is active (thereby creating a breeze to speed evaporation).

Less consistent or less forceful cooling is acceptable.

The use of fans and batteries are undesirable or unacceptable.

When consistent, maximum cooling is needed, forced-air embodiments provide an ideal solution to the problem of maintaining maximum cooling comfort in hot temperatures. Forced air embodiments fall into two categories: 1) embodiments in which an external air barrier to confine airflow to the area surrounding elements 120 is integrated, and 2) embodiments in which an existing article of clothing, accessory, or piece of gear is used as the external air barrier. The former is discussed as Expression #2; the later will be discussed later as Expression #3.

FIG. 5a illustrates a simple forced air embodiment for cooling the forehead. Comparing this with FIG. 2a, it can be seen that two things have been added: 1) an air space 165 adjacent and parallel to the user's skin formed by an outer barrier 160 into which elements 120 penetrate, and 2) means to propel air through the space, such as with a fan 170, batteries 172, and switch 171. Outer air barrier 160 can be made of any flexible and preferably elastic material that restricts airflow to the region around elements 120, and can be water-resistant or absorbent. This is the essence of all the forced-air embodiments.

Expression #2

Operation of Integrated Forced Air Embodiments

Referring to FIG. 5a, to operate, the user will wet reservoir 100, place skin-facing surface 125 of the device against the forehead, wrap the ends of the device around the head, then secure the ends together with hook-and-loop fasteners 131 or any other fastener, such as a snap, clip, button, or catch. FIG. 5b shows the device in place on a user's head. The water in reservoir 100 will rapidly migrate by capillary action onto fluid-wicking surfaces 124 of elements 120. The user will then turn switch 171 to the "on" position, which connects battery 172 with fan 170. Fan 170 pulls air into the device through intake vent 166, through the length of air space 165, and out through fan 170, circulating air around all of elements 120. As air moves around elements 120, the water on fluid-wicking surfaces 124 readily evaporates, carrying heat from the user's forehead through elements 120 and out into the surrounding air.

Expression #2

Additional Integrated Forced Air Embodiments

FIG. 5c depicts a forced-air embodiment that cools the forehead as well as the scalp around the sides and back of the head. As previously described, a fan 170 is provided, along with a plurality of elements 120 that penetrate reservoir 100 into air space 165 formed by barrier 160. In this embodiment, the skin-facing surfaces of elements 120 around the sides and back of the head have the same kind of rounded, rod-like extensions described for the fan-free baseball cap (FIG. 2i) and the dog cooler (FIG. 2l). FIG. 5d shows how cooling element extensions 123 bring cooling relief to the user's scalp 152 by penetrating user's hair 151. The entire device is elastic and in this case, barrier 160 is water-wicking, so the user need only wet the outside of the device, pull it on over the head, and turn on fan 170. Air is drawn in through vents 166 and out through the fan. Edge barrier 161 forces the air to move past all elements 120.

FIG. 5e shows the device embodied as a forced-air cooling vest. The principle is the same as depicted in the cooling headbands described above, but here reservoir 100 and elements 120 cover the user's entire torso. Additional fluid reservoirs 110 provide centralized locations for the user to insert water, which migrates throughout the device, feeding moisture to elements 120. Additional fluid reservoirs 110 provide an easy way to wet the device. Sponge 112 has notch 114, which increases sponge surface area, allowing it to absorb water as quickly as it is being inserted. A user would insert the tip of a water bottle into reservoir opening 221 and squeeze; the water will move through notch 114, rapidly wetting sponge 112, and, through capillary action, will also wet all of reservoir 100. Fans 170 draw air into the device through air intake vents 166 at the edges of the vest and circulate air through air space 165, speeding evaporative cooling from elements 120.

Backpackers have the problem of needing to cool their back, but unless the backpack is held away from their body by a frame or spacer, the fan cannot be located on the back because it would be blocked by the pack. In this case, a vest such as the one depicted in FIG. 5e would keep the user cool. Such a device can have one or more fans located on the sides, front, top edges, or bottom edges of the device. An embodiment for backpackers might need to integrate means to prevent the backpack from putting undue pressure on the elements 120. This can be accomplished by inserting cushioning material between outer air barrier 160 and the backpack, or by inserting a stiff material that will distribute the weight of the pack across a larger area of elements 120.

FIGS. 5f and 5g show reservoir 110 from above. Reservoir 110 interfaces with elements 120 either by sitting on top of elements 120 as in FIG. 5f, or by sitting directly on reservoir 100 as in FIG. 5g. If reservoir 110 is sitting on the tops of elements 120, wicking material 118 is used to contain water as it is being poured into reservoir 110 through notch 114, while also distributing it across the tops of elements 120.

In all Expression #2 embodiments, outer air barrier 160 itself can fulfill the function of additional fluid reservoir 110 simply by making it of a wicking material. Such a wicking material can also be coated with a waterproof material either to prevent water from evaporating directly in the surrounding air or to prevent the outside of the device from wicking water onto anything the user may be leaning against.

FIG. 5h shows the device embodied as a forced-air baseball cap. Comparing this with FIG. 2i, what has been added is barrier 160 forming an air space over elements 120, and a fan with batteries and a switch. Fan 170 is placed in the ideal location at the top center of the hat, where it can draw air equally from all intake vents 166. The user wets the cap, puts it on, and turns on the fan. Cooling element extensions 123 on the bottoms of elements 120 (not shown) penetrate through the hair and touch the scalp, cooling the user's head. Additional reservoir 110 can be provided in the form of the visor, which can be made of a slightly stiff, but rapidly wicking material, such as a porous plastic, or felt with a stiff backing.

FIG. 5i shows a forced air blanket embodiment. Fan 170 can be run using either battery 172 or power from a wall outlet. The user would add water to additional reservoirs 110, turn on fan 170, and enjoy cooling comfort all night. If needed, a very thin piece of soft fabric can be provided to keep skin-facing surface 125 of the blanket (not shown) from touching the user's skin, making it feel cozier to the user.

Just as with clothing, the idea that a blanket can actually cool, rather than warm, a user may seem fairly radical. Once the idea is embraced, however, it's easy to see how this method can easily be applied to shawls and wraps. People are often uncomfortably hot and may not wish to change into clothing embodiments of the device to get cooler. In such instances, using a fan-free or forced-air embodiment such as a shawl, scarf, or wrap can bring welcome, cooling relief.

A forced-air pet cooler very similar to the version depicted in FIG. 2l can be created by adding an air space 165 adjacent and parallel to the animal's fur (created by outer air barrier 160), one or more fans 170 to propel air through space 165, and elements extensions 123.

Expression #2

Forced Air Embodiments as Protective Gear

In situations where consistent, maximum cooling is needed along with hazard protection, forced-air embodiments can be created in which outer air barrier 160 is made of whatever material is necessary to protect the user from physical, thermal, chemical, biological, or radioactive hazards. If double or triple protection is needed, outer reservoir barrier 101 and/or inner reservoir barrier 102 can also be made of whatever protective material is needed. If quadruple protection is needed, reservoir 100 can itself be made of any flexible and absorbent protective material, which is preferably also elastic.

In protective garments to be used in extremely hazardous situations, the device may need to keep external air from touching the skin of the user. For these devices, the entire air stream as it enters the device, travels around elements 120, and exits the device, must be isolated from the user's skin as well as the air the user is breathing.

FIG. 5j shows an integrated forced-air embodiment providing physical protection for bikers. This device uses leather as outer air barrier 160, which forms motorcycle jacket shell 184. Fan 170 is located in the middle of the back, and air intake vents 166 are located near all edges of the device. Beneath motorcycle jacket shell 184 is an inner layer like that depicted in FIG. 2c, with reservoir 100 studded with elem 120. This inner layer can be attached, not attached, or detachable from jacket shell 184. The user wets the inner layer, puts the device on, turns on fan 170, and enjoys cooling relief whether in motion or not.

Construction workers, cyclists, and other people wearing helmets would also appreciate being cooled in hot weather. FIG. 5j depicts a forced-air hard hat embodiment. It is essentially the same as the forced air baseball cap in FIG. 4h except that the outer air barrier is replaced with the stiff shell of hard hat 181. The device has an inner cap studded with elements 120 having extensions 123. To this, suspension straps 180 are added, which function exactly as they do in normal hard hats, creating a safety zone around the user's head. Suspension straps 180 can be an integral part of the inner cap, and elements 120 can be penetrate through suspension straps 180 as well as the inner cap that is acting as reservoir 100. As in a normal hard hat, suspension straps are attached to the outer shell of hat 181 at intervals. The user wets reservoir 100, puts on the device, and turns it on. As fan 170 activates, it draws air in around the edges of the device (functioning as intake vents 166), over elements 120, and out through the fan, cooling the user.

FIG. 5k shows a motorcycle helmet embodiment. Helmet 182 has a thick layer of foam padding 183 inside, which can double as additional fluid reservoir 110. Water can be added from the bottom side of elements 120 (with cooling element extensions 123 now shown) or through one or more holes in the top of helmet 182. As water soaks through foam padding 183, it migrates onto and across fluid-wicking surfaces 124 of elements 120, and into primary fluid reservoir 100. When the user turns on fan 170, air is drawn in through air intake vents 166, across elements 120, and out through fan 170, cooling the user's head. In another variation, elements 120 are attached directly to foam padding 183, eliminating the need for reservoir 100 as a means to support elements 120. In this configuration, foam padding 183 itself acts as the primary fluid reservoir and, because of its thickness, can hold a tremendous amount of water.

Expression #2

Automated Forced Air Warming/Cooling Devices

FIG. 5m depicts a thermostat-controlled jacket. Thermostat 140 is connected to a temperature sensor 141 on the inside of the device, a control circuit 142, and fan 170 (not shown; in the center of the back). When a user sets the thermostat to a desired temperature, control circuit 142 will respond as follows:

If the user's skin is currently at a temperature above that set on the thermostat, control circuit 142 will turn on fan(s) 170, cooling the user's skin.

If the user's skin is currently at a temperature below that set on the thermostat, control circuit 142 will turn off fan(s) 170, stopping the cooling action, and, by making use of the thermal insulating effect of all the materials in the device along with air space 165, will warm the user's skin.

If control circuit 142 turns off fan(s) 170 to stop the cooling action, it can also trigger the blocking of all open edges of the device with controllable edge air barriers 162 to speed the internal warming of the device. Controllable edge air barriers 162 can be opened or closed by any suitable means, such as by inflating plastic "balloons" along the edges, thereby sealing the air vents, or by using mini servo-motors, linear actuators, or nitinol-type wires (or other material that expands or contracts with the application of an electrical charge) to mechanically slide or close flaps. The edges might also be blocked without the use of a control circuit by using vents with very lightweight flaps that stay open only when a fan or other air-moving device is forcing air through them.

A similar effect can also be achieved without the use of a control circuit. Thermostat 140 can be used as a mechanical switch for fan(s) 170 in the same manner that analog thermostats control home furnaces. But an advantage of having a control circuit is that it can sense the rate of change of the user's skin temperature and adjust the speed of fan(s) 170 accordingly, thereby creating a stable thermal environment that does not subject the user to rapid changes in temperature that would result if the device is either on or off. This will be a great boon to users who are extremely sensitive to sudden or even slight temperature changes.

Referring to FIG. 5n, by adding extra thermostats 140, fans 170, controllable edge air barriers 162, and internal air barriers 163, a warming/cooling jacket can be made with a number of automatically-controlled zones that respond to the different thermal needs of different parts of the body. Such a device need not add extra reservoirs 110 because water can migrate into different thermal zones without interrupting internal air barriers 163. This approach will be useful for anyone whose body tends to get colder is some areas more easily than others.

Barriers 162 can be closed manually by blocking the air intake and exhaust areas. This can be accomplished by tightening a drawstring, closing a flap, zipping two flaps together, clipping one part to another, etc. Options that can be activated either manually or automatically include pivoted flaps, sliding flaps, rotating vents, interconnecting cells with parallelogram shapes that stand up or collapse as a unit, and inflatable "balloons", etc.

If, in a thermostat-controlled embodiment, outer air barrier 160 were itself a thermal insulator (such as down, wool, fleece, fur, synthetic insulation, etc.), the range of temperatures that a warming/cooling jacket (or any other embodiment) can accommodate is greatly increased. When the jacket is in cooling mode, an insulated version of outer air barrier 160 would keep hot air and sunlight from mediating the cooling effect of the device, thereby increasing its efficiency. When the jacked is in warming mode, an insulated version of outer air barrier 160 would more efficiently retain the user's body warmth. Such a warming/cooling jacket can automatically keep a user comfortable year-round in either hot or cold weather. The warming/cooling approaches described in this section would apply just as well to all other embodiments mentioned, such as clothing and accessories for humans, protective garments, embodiments for pets and other animals, blankets and wraps. For example, by simply adding one or more thermostats 140, sensors 141, and control circuits 142, the forced-air blanket embodiment shown in FIG. 5i, a user can be kept at a pre-set comfortable temperature all night.

Expression #2

Alternative Configurations

Reservoir 100, elements 120, inner and outer reservoir barriers 101 and 102, and outer air barrier 160 can appear in a different order than previously shown. FIG. 5o shows an edge view of a section in which bottoms of elements 120 are touching the skin as before, but the next layer in the system is stabilizing fabric 103 instead of reservoir 100. Stabilizing fabric 103 can be any fabric that is flexible (and preferably elastic), and has the primary function of holding elements 120 stable relative to each other. In the configuration shown, this function is very important, because if reservoir 100 were not highly elastic, when the device is curved around a body part, the skin-facing portions of elements 120 would be forced closer together, and can potentially pinch the user's skin if stabilizing fabric 103 weren't there to hold them apart. FIG. 5p shows that a simple way to mediate the pinching effect is to make the skin-touching parts of elements 120 curved and not use fabric 103.

Stabilizing fabric 103 can be an open mesh and can also be partially or completely closed or watertight. If it is an open mesh, or, as in FIG. 5p, fabric 103 is not used, when fan 170 is on and air is moving through air space 165, air will move between the heads of elements 120 and speed the evaporation of any perspiration on the user's skin, which might be an advantage in some applications. In this configuration, the combination of outer reservoir barrier 101, reservoir 100, and inner reservoir barrier 102 will perform the function fulfilled by outer air barrier 160 as show in previous Expression #2 embodiments; it will define the top of air space 165, confining the forced air to the spaces between elements 120. This configuration also has the advantage of making it easier to wet reservoir 100 because it is closer to the outside of the device. For example, additional reservoirs 110 can be attached directly to the surface of reservoir 100 in a number of locations.

FIG. 5q shows another option in which reservoir 100 is used both at the tops and the bottoms of elements 120. In this configuration, only one of the two reservoirs would need to be wet by the user because water from one would wet the other by migrating through elements 120. Migration can be speeded by providing one or more wicking materials as bridges between the two layers. Such bridges would have to be intermittent so as not to block air from moving through air space 165.

Although additional layers of fabrics, barriers, or reservoirs can be placed at levels between the tops and the bottoms of elements 120, there would probably be no advantage. Doing so would cause many disadvantages, including:

- It would create extra air spaces 165 that would require ventilation
- Drag and turbulence from the extra surfaces would increase resistance to airflow
- The device would be rendered more expensive and less effective.

Expression #2

Design Considerations

A concern that must be addressed in all forced air embodiments is the possibility of the formation of mold or mildew between the layers of the device. The fact that outer air barrier 160 restricts airflow to the space surrounding elements 120 is good for maximizing cooling, but also good for trapping moisture inside the device when not in use. For this reason, reservoir 100, outer air barrier 160, and any other layers of the device (including inner reservoir barrier 102 or outer reservoir barrier 101) can be impregnated with a chemical that will suppress the formation or mold or mildew. Additionally, the user can be instructed to remove outer air barrier 160 and/or keep fan 170 on until the device has thoroughly dried before putting it away.

Fan 170 can draw air in from the outside and push it through the device and out the edges, or it can draw air into the device from the edges and out through the fan. However, if the fan is pushing air into the device, it will tend to cause outer air barrier 160 to billow away from elements 120, which might look unappealing. For this reason, configuring the fan(s) to pull air through the device and out through the air is considered a superior solution.

If for any reason fans should need to push air into and through the device, there are several ways to prevent outer air barrier 160 (or any pre-existing outer garment worn over an embodiment designed to accommodate existing garments as described under Expression #3) from billowing away from the device, including the following:

- Outer air barrier 160 can be attached to the peaks of elements 120, either permanently or removably (such as with a permanently tacky surface glue).
- Fan(s) 170 need not be so strong as to billow outer air barrier 160.
- A number of slow-moving fans 170 can be employed around the device to keep the air moving without causing undue billowing of outer air barrier 160.

For the device to be most effective, a sufficient volume of air must flow from intake to exit across all of elements 120. Unless the fan or fans are situated in the middle of an area of elements 120 (in most embodiments, this is often impossible or impractical), the device will need one or more permanent edge air barriers 161 to block too much air from entering or exiting any one region of the device at the expense of other regions. FIG. 5a shows permanent edge air barriers 161 on both long edges of the device, forcing the air to move all the way through both ends of the device for maximum cooling.

Outer air barrier 160 not only bounds the space around elements 120 to restrict airflow, but visually hides elements 120, providing the possibility of virtually unlimited fashion options. Outer air barrier 160 can be made replaceable, allowing users to buy one base unit and as many outer coverings as suits their needs and desires.

Forced air embodiments can be created for any body part using corrugated elements 126 or deformed elements 127 described under Expression #1 simply by adding at least an outer air barrier 160 and a fan 170 or other means to move air through the resulting spaces.

Expression #3

Forced Air Embodiments for Use with Existing Articles

Expression #3 of my cooling system comprises a group of embodiments in which the function of outer air barrier 160 is fulfilled by an existing article of clothing or piece of gear. FIG. 6a shows a device designed to be worn under an existing T-shirt. It is very similar to the fan-free embodiment shown in FIG. 2c, except also provided is fan 170, as well as a battery and a switch, not shown. Missing is integrated external air barrier 160 provided with all Expression #2 embodiments.

Referring to FIG. 6b, the user puts the device on, wets reservoir 100 (thereby wetting elements 120), then puts on existing T-shirt 164 and turns on fan 170. Fan 170 draws air in through intake vents 166, through air spaces 165 formed between reservoir 100 and existing T-shirt 164, and out through the fan. To prevent water from wetting the T-shirt, tiny dots or areas of waterproof plastic can be applied to the tops of elements 120.

FIG. 6c shows an embodiment designed to be used with an existing hat or cap. Fan 170 is on the edge of the device so it won't be blocked by the user's headwear. The user wets reservoir 100, puts on the device, then puts his or her own existing hat or cap 168 over it. When the user turns the device on (battery and switch not shown), fan 170 is activated and begins to circulate air around elements 120, promoting evaporative cooling. Cooling element extensions 123 on the bottoms of elements 120 are not shown.

Embodiments can be created to work with existing articles of protective gear. For example, an existing chemically resistant suit can perform the function of outer air barrier 160 by slipping it over an embodiment of the device designed to provide proper air circulation for that specific suit.

As an example of an article designed for physical protection, a device can be made to accommodate a biker's existing leather jacket. Such a device should not place a fan in any location that would be blocked by the jacket; one or more fans would have to be located at the bottom or top edges of the device, and possibly also at the ends of both sleeves.

CONCLUSION AND RAMIFICATIONS

From the above descriptions and drawings, it can be seen that my flexible evaporative cooling system clearly improves on prior-art personal cooling systems while simultaneously making possible a whole new range of personal thermal comfort devices. It delivers a powerful, long-lasting cooling effect directly to the skin of a human or animal user, without requiring the user to hold the device or expend any effort. It does not need to wet the user's clothing or skin. It requires little or no battery power to run (none in the fan-free embodiments). It is flexible, and can therefore be worn comfortably on or against a user's body. It can be easily adapted for use on pets and other animals. It can be embodied as clothing, accessories, uniforms, and protective garments. It can be worn under a backpack, motorcycle leathers, or under other garments, uniforms, or protective gear, and it can be used as a sheet, blanket, scarf, or shawl. It can even be embodied as a variety of automated, thermostat-controlled, personal warming/cooling devices.

Some of the many far-reaching ramifications of my cooling system include its ability to:

- Allow users to wear heavier clothing than they would otherwise be forced to wear in hot weather, while remaining cooler than if they had worn nothing at all.
- Provide cooling relief for people engaged in minimal activity such as working in an office or driving, as well as people engaged in walking, running, jogging, hiking, basketball, baseball, summer sports, golf, traveling, sight-seeing, etc.
- Open a whole new range of weather-independent fashion options for users.
- Give people more control over their personal comfort all year round, in hot or cold temperatures, inside and out.
- Reduce reliance on air conditioners.
- Allow users to work and play longer in hot temperatures than they would otherwise be able to tolerate.
- Allow users to live in hotter climates than they could previously tolerate.
- Allow people to own fewer clothes, if they so desire.
- Permit travelers to bring fewer clothes on trips, if they wish.
- Provide cooling relief for sufferers of first-degree burns, such as sunburns.
- Provide means by which sunburn victims can simultaneously cool the burned portions of their skin and warm the unburned portions (using multi-zone Expression #2 devices).
- Provide protection from mosquitoes and other insect pests. According to the World Health Organization, there are at least 50 million annual cases of insect-borne diseases, many of which are fatal.
- Protect users from overexposure to solar UV radiation while remaining cool and comfortable. Approximately 130,000 malignant melanomas and 66,000 deaths occur globally each year, substantially contributing to mortality rates in fair-skinned populations.
- Provide significant thermal comfort while helping thousands of people survive in extremely hot weather. Every year, tens of thousands of people worldwide die from heat waves. In the summer of 2003, heat waves in Europe killed more than 19,000 people and uncounted thousands of animals. Estimates of the future effects of global warming consistently point to increasing extremes, with even more devastating heat waves.

SCOPE OF THE INVENTION

Many variations on the embodiments described above can be employed within the intended scope of the invention, as elaborated below.

Reservoir 100 can:
Be made of anything flexible and absorbent (and preferably elastic), such as:
- A single layer of flexible, absorbent material (made porous with woven or nonwoven fibers, hydrophilic pores, tiny grooves, or pits).
- Two or more layers of different absorbent materials.
- Trapped layers of absorbent beads.

Be thin, but the thinner it is, the less fluid it will hold.
Be any shape, so long as it maintains wicking contact with elements 120.
Have holes at intervals to allow the user's skin to breathe more readily.
Have antimicrobial and/or antibacterial properties to prevent the formation of mold, mildew, or other undesirable organisms.
Be impregnated with additives of any kind, including salts, surfactants, oils, and/or fragrances.
Contain include a number of horizontal moisture boundaries to counteract the effects of gravity, preventing most of the fluid from settling toward the bottom of the device. In this approach, once water is introduced into the material, it can only migrate to the nearest moisture boundary, preventing a wide gradient of saturations and insuring that moisture is available to elements 120 that are closer to the top of the device.
Be positioned anywhere in the device, as long as it imparts fluid to elements 120.
Be in more than one piece, but if so, means must be provided whereby all pieces can be moistened. Multiple pieces can be connected in any suitable manner (such as being sewn, pressed, glued, or flame-laminated, or connected by wicks, capillary tubes or channels) so that water migrates between them. Separate pieces of reservoir 100 can be wet through separate reservoirs or fluid collection and distribution channels. Alternatively, separate pieces can be wet by spraying or dunking the entire device in water.

Reservoir barriers 101 and 102 can:
Be made of any material suitable to meet the needs at hand. For example, if it is being used to:
- Seal reservoir 100 from allowing moisture from evaporating from within the device, it should be watertight;
- Protect reservoir 100 from being abraded by use, it should have abrasion-resistant properties;
- Protect reservoir 100 from UV radiation, it should have UV-blocking properties;
- Create a fashion statement, it should be easy to print, stitch, or flock a design on it;
- Create a feeling of softness to the user's skin, it should have a soft skin-facing surface 125;
- Help wick perspiration from the user's skin to reservoir 100, it should be highly absorbent.

Be adhered to fluid reservoir 100, can be pressed against reservoir 100 without being adhered, or can be added to reservoir 100 as a coating.
Be omitted entirely and the device will still work. Without one or both barriers:
- Water might leak onto the user's skin or clothing;
- Water will evaporate directly off the surface of reservoir 100, reducing the effectiveness of the device;
- Reservoir 100 might become abraded by normal wear External reservoir 109 can:
Be provided as an integral part of the cooling system or not;
Be made attachable and detachable from the device;

Have a pointed applicator tip that engages with opening 221 in additional reservoir 110 so that it forces open a part of reservoir 110, allowing reservoir 110 to function without a cap;

Be any size, shape, color, or number.

Additional reservoir(s) 110 can:

Be made of anything that holds and/or absorbs water;

Be hard or soft;

Be clear, translucent, or opaque;

Have walls composed of any watertight (or fluid-resistant) material or not;

Be filled or not with absorbent material, such as a sponge;

Be itself a sponge;

Have an openable or removable cap to prevent water from spilling;

Be any number, shape, color, or size;

Be located anywhere on the device;

Be removable from the device for easy wetting;

Be located off the device (in the form of a purse, shoulder bag, knapsack, fannypack, etc.), but connected with reservoir 100 by fluid delivery means such as a wick;

Be simply a pattern of thicker areas on reservoir 100 or a pattern of one or more different materials attached to or as extensions of reservoir 100. In either case, such raised areas may not necessarily need means for the user to wet them directly; they can get wet through contact with other wet areas;

Be located at the bottom edge of a shirt or jacket embodiment and can take the shape of a belt;

Be located at the top edge of a shirt or jacket embodiment and can take the shape of a collar;

Not only look like a belt, but perform the function of a belt. The belt would preferably not need to be threaded through loops and can be attached with any kind of fastener.

Elements 120 can:

Be made of any thermally conductive material. If metal, it can be any alloy or laminated combinations of alloys and it can be plated or coated with any other material or process that does not prevent the microgrooves or other wicking interstices from wicking fluid in the areas where wicking is needed (on skin-facing surface 125, wicking may not be desirable). If aluminum, it can be anodized to protect the surface from salts, or plated with, say, nickel, to protect the user from absorbing too much aluminum through skin contact.

Be any number, size, shape, or color, provided they conduct heat, wick water on at least portions of their surface, and allow the device to be flexible.

Be composed of mixed shapes, sizes, and colors, within any device.

Be connected to each other by any flexible means, including:

Being attached to a flexible material that might or might not be absorbent and/or continuous.

Being attached with any flexible material, such as rubber, vinyl, fabric, sponge, etc. that might or might not be absorbent or wicking.

Using a portion or extension of the material or materials that comprise elements 120 that is itself used to make connections with other elements.

Using a flexible connector, such as a spring or hinge.

Themselves be flexible.

Be arranged in any pattern whatever.

Be arranged in any density, and density can be varied according to the needs of different body parts. The farther apart they are spaced, however, the less cooling they will provide.

Emerge from reservoir 100 at an angle, allowing the fins to retain length for cooling power, while taking minimal vertical space.

Be oriented in any direction, but should be positioned so as to promote maximum airflow across the fins.

Be quite short, keeping the cross-sectional profile of the device to well under a quarter of an inch (in some cases, approx. one eighth of an inch). Although restricting the length of the fins would reduce the heat pump effect, the trade-off in favor of less bulk would be attractive to many users. Better yet, the fins can be longer, and formed into a shape that takes little vertical space.

Be made of two or more parts that connect. Care must be taken to ensure that such parts tightly mate so that heat can move efficiently between them.

Have one or more downward, skin-facing extensions designed to get through human hair or animal fur to deliver cooling relief to the user's skin.

Be coated or flocked on skin-facing surface 125 with any material to change its feel to the user's skin, to prevent fluid from leaking or wicking onto the user's skin, and/or to make skin-facing surface 125 of the device washable, as long as the coating or flocking does not significantly thermally insulate elements 120 from the user's skin. To reduce the thermally insulating effect of such a coating, it can be filled with a thermally conductive powder, such as aluminum.

Fluid-wicking surfaces 124 of elements 120 can:

Cover all or part of elements 120, including any surfaces.

Touch the user's skin or not. If a wicking surface is in contact with the user's skin it will wick up the salty water of the user's perspiration and combine it with the fresh water in the reservoir, eventually leaving deposits of salt on the surface of elements 120. Theoretically, this may not be a problem; the user can simply douse or spray the device with warm water to dissolve the salt. In practice, if aluminum is used for elements 120, its surfaces may be corroded by the salts, which can negatively affect device performance. To avoid this issue, the portions of elements 120 that are in contact with the user's skin can be left untreated so they will not wick water. Touch outer air barrier 160 or not. To prevent wetting of outer air barrier 160 (especially if an existing garment is fulfilling the function of outer air barrier 160), those portions of elements 120 that are in contact with outer air barrier 160 can be left untreated so they will not wick water.

Temperature control system (thermostat 140, temperature sensor 141, and control circuit 142) and other electronics can:

Be analog and/or digital.

Have built-in intelligence that considers skin temperature, outside temperature, and humidity, keeps records of the user's past thermal preferences, and can thereby control skin temperatures in ways that anticipate the user's needs. GPS data can also be integrated so the system is able to check local weather conditions and/or know if the user is inside a building.

Control each fan in the device separately or all together.

Control each of the controllable edge air barriers 162 separately or all together.

Include a "power on" indicator, such as an LED.

Include a "low battery" or battery charge status indicator.

Include a two-color LED to indicate "power on" with one color and "low battery" with the other color.

Communicate electronic information (such as "low water" status) with the user via any suitable means, including lights, sounds, vibration, visual displays, or voice.

Include a low-medium-high or variable power switch for varying the fan speed according to the user's needs.

Provide one or more digital or analog thermometers, enabling the user to monitor air and/or skin temperatures at one or more locations or zones around the device.

Be made removable, allowing the user to launder the device.

Be placed anywhere on or off the device. If off the device, it can communicate with the device by wire or wirelessly.

Use wireless communications between sensors and control circuits to avoid complications in wiring.

Use wireless communications between itself and a user's devices.

Outer air barrier 160 can:

Be made of two or more layers of any suitable materials.

Be made, at least in part, of an absorbent material, adding extra water reservoir capacity as well as extra thermal insulation. For example, it can have an absorbent inner-facing layer and an impervious outer-facing layer.

Be made of a transparent material to show off the inner workings of the device.

Be affixed to the tops of elements 120 either permanently or temporarily, or can rest against the tops of elements 120 so that it can shift laterally as needed.

Be made removable and replaceable with different outer shells.

Avoid touching the tops of elements 120; means can be used to separate it from elements 120 so that air can flow over the tops of elements 165.

Air space 165 can:

Be any height practical, but more than one quarter of an inch is probably not needed, except in unusual cases.

Be not perfectly uniform in height, but must allow forced air to move freely around elements 120.

Fan(s) 170 or other air-moving means can:

Be any number within a device.

Be in any location on the device.

Be in any position relative to outer air barrier 160. If it is under air barrier 160 (inside of air space 165), it can be arranged to pull air from one side and push air toward the other, causing air to move through the device. It need not intake or exhaust air directly to the outside.

Be made waterproof and/or detachable to protect from being wet when the user adds water or washes the device.

Be replaced by any type of fan or blower impellers, including radial, axial, and tangential, and different types can be combined within a device.

Be replaced by any air moving means, including electrostatic or piezoelectric, although to date such means are not sufficiently powerful or efficient for use in a battery-operated device.

Be any number within a device.

Fluid delivery means:

If capillary type, can be made of:
 Any absorbent material that allows fluid to migrate by capillary action;
 Any material in which tiny grooves can be cut, molded, or impressed, that will transport the fluid by capillary action;
 One or more tubes, channels, or shapes that will transport the fluid by capillary action.

If gravity-fed type:
 Additional reservoir 110 will need to have:
  A cap that is openable or removable;
  A tiny vent hole or, better yet, a porous plug that will allow air in, but wouldn't let water out, so as to avoid creating a low pressure zone inside additional reservoir 110, and so stop the water from flowing out;
  Any type of valve at the bottom to allow fluid to exit. Valves can be manual or automatic and can be powered by any suitable means.
 Tubes or channels can be any workable size, shape, color, or number.

Power for electronics and/or air-moving means can be provided by any means, including:

Any type of battery, including rechargeable.

Battery or other electric power source can be off the device (for example, in a pocket) and connected by wire to the air-moving means.

Fuel cells.

Solar power (avoids the problem of running out of batteries, but is problematic in cloudy and nighttime conditions and may not provide enough power to move sufficient air.

Manually winding a spring (beneficial both to avoid problems with wetting electrical or electronic components and the problem of running out of batteries).

Automatically winding a spring, using energy harnessed from the user's motion.

Winding a spring using a motor (can compress a lot of energy, but can be hard to wind manually in the field).

Using compressed air or gas (avoids the problem of wetting electrical components, but requires special gas cartridges).

Combining a manual wind-up mechanism with a motor-driven and automatic winding from the harnessed motion of walking or running. For example, the main spring can be wound at the user's home with a motor, and its energy can be supplemented by the motion of walking or running. If the spring winds down while the user is away from home, he or she can wind it manually.

Manual pump-activated compressed air (such as used for pellet guns).

Any form of energy can be converted into any other form to power the device. For example, hydrogen can be converted via a fuel cell to electrical energy, which in turn can power an electric fan.

Low water detection and alert systems can include:

Chemicals that change color when wet can be used in any of the reservoirs or capillary delivery means as a visual indicator of low water.

Electronic water detection means can be provided along with alerting means, which can include auditory alarm, flashing light, vibration, and voice notification.

The system can send a "low water" alert (or any other system information) to any device the user may be interacting with, (such as a personal computer, a palm computer, cell phone, etc.) which can display the alert to the user.

The cooling fluid can be varied as follows:

Water is best as the cooling fluid because it is nontoxic, easy to acquire and use, and many people keep some water handy for drinking.

Alcohols can be used as the cooling fluid, since many evaporate more readily than water. However, the fumes of the evaporating alcohol would likely have negative consequences for the user and others in the environment Volatile hydrocarbons or other rapidly evaporating solvents can be used, but nearly all would have potentially serious adverse health effects and/or be very expensive.

Additives to water can be employed, including salts, alcohols, and surfactants to speed capillary action and/or evaporation rates.

Fragrances can be added for the user's pleasure, for aromatherapy, or as a way to be alluring to others without having to apply scents directly to one's body.

Other variations are possible:

A thin, inner fabric shell or lining can be provided to cover the skin-contacting heads of elements 120. The shell would serve the functions of protecting the device from being soiled by the user's skin oils and perspiration, being washable, and protecting extremely sensitive users from the feeling of the heads of elements 120 against their skin. The thinner is the inner fabric shell, the less it will reduce the cooling effect from reaching the user's skin. To minimize the thermally insulating effect of such a lining, it can be filled with a thermally conductive powder, or made with thermally conductive fibers.

Fan(s) 170 or other air-moving means can be attached to any layer and/or be made removable, so outer air barrier 160 can be washed or soaked.

On forced-air versions, whatever layer is outermost, if it is stiffer than the others (yet still flexible), it can be considered to be a housing. Such a housing can protect the user and elements 120 from outside objects and forces.

The outermost layer can be impact resistant, and even bullet-proof, as long as it remains flexible. It can be made of a plurality of small pieces that interlock and/or overlap in the manner of fish scales, and/or can include wire mesh for physical protection. Elements 120 themselves will provide some physical protection.

Overall configurations can be varied as follows:

Using the same methods and approaches already described, devices can be made for cooling objects other than humans and animals. For example, by simply changing the shape of any of the fan-free or forced-air devices already illustrated, devices can be made that cool soda cans, candies that easily melt in hot weather, steering wheels, computers, or anything whatsoever that would benefit from staying cool or would benefit a human or animal user of such objects.

Devices can be made that combine units for cooling several parts, such as head, forehead, and neck, and each section can be made detachable from the others. A jacket can be made with a detachable neck cooler portion, and detachable upper and lower arm coolers. Pants can be made with one or more pairs of detachable lower portions, allowing the user to create shorts of varying lengths as needed.

A suit can be made of many parts or pieces to be attachable and removable from each other. For complete thermal protection, a whole-body suit can be made in which each part or section can be removed.

Fan-free and forced-air embodiments can be combined in different areas of the device.

The composition of any layer of the device can be different from one part of the device to another.

Means can be provided (such as using springs and/or springy foam) to urge the device against the center of the back where it indents at the backbone, so that elements 120 can maintain skin contact.

Other heating and/or cooling means can be added to the device, such as electric heating elements, thermoelectric devices, heat pumps, etc., to extend the heating or cooling potential of the device.

Other devices, such as radios, TVs, computers, audio/video recorders/players, cellular and cordless telephones, GPS systems, etc. can be incorporated into any embodiment.

Devices can vary in size, shape, color, and design, and still fall within the intended scope of the invention. The major elements can be put in different positions than shown (e.g., batteries can be located where a water reservoir is depicted, etc.). Thus, the scope of the invention should be determined by the descriptions given above, along with the appended claims and their legal equivalents, rather than by the examples given alone.

I claim:

1. A device for cooling the skin of a human or animal user, comprising:
    a) A plurality of metallic thermally conductive elements, each promoting fluid to absorb into and wick across at least portions of a surface or surfaces of the elements by capillary action,
    b) one or more flexible hydrophilic fluid reservoirs,
    c) means for said thermally conductive elements to penetrate or be maintained in contact with said flexible hydrophilic fluid reservoir so that fluid will tend to migrate from said flexible hydrophilic fluid reservoir onto and across said fluid-wicking surface of said thermally conductive elements, and
    d) means for maintaining one or more portions of said thermally conductive elements in contact with the user's skin,
    whereby when said flexible hydrophilic fluid reservoir is wet and one or more portions of said thermally conductive elements are in contact with the user's skin, heat from the user's skin is transferred through said thermally conductive elements, to the evaporating fluid, and into the surrounding air, thereby cooling the user.

2. The device of claim 1 wherein each thermally conductive element
    a) has a "U" shape,
    b) extends through slits in said flexible hydrophilic fluid reservoir that are either precut or that are created as each element is pressed through said flexible hydrophilic fluid reservoir, and
    c) has two ends that are curled in toward the bottom inside of the "U" in the manner of a staple,
    whereby said thermally conductive elements are mechanically affixed to said flexible hydrophilic fluid reservoir.

3. The device of claim 1 wherein said flexible hydrophilic fluid reservoir is coated with or protected by one or more barriers designed to prevent moisture in said fluid reservoir from evaporating directly into the surrounding air or wetting the user's skin, or to prevent physical, chemical, biological, thermal, or radiological hazards from damaging the device or the user.

4. The device of claim 1 further providing means to store and transport additional fluid to said fluid-wicking surface or surfaces.

5. The device of claim 1 wherein the skin-facing surface of said thermally conductive elements have one or more thermally-conductive post-like extensions with rounded ends designed to penetrate human hair or animal fur and touch the user's skin.

6. A device for cooling the skin of a human or animal user, comprising:
- a) a plurality of metallic thermally conductive elements, each promoting fluid to absorb into and wick across at least portions of a surface or surfaces of the elements by capillary action,
- b) flexible or elastic means interconnecting said thermally conductive elements,
- c) means for wetting the fluid-wicking surfaces of said thermally conductive elements, and
- d) means for maintaining one or more portions of said thermally conductive elements in contact with the user's skin, whereby when said thermally conductive elements are wet and one or more portions of them are in contact with the user's skin, heat from the user's skin is transferred through said thermally conductive elements, to the evaporating fluid, and into the surrounding air, thereby cooling the user.

7. The device of claim 6, further including means for storing and transporting additional fluid to said fluid-wicking surface or surfaces.

8. The device of claim 6 wherein the skin-facing surface of said thermally conductive elements have one or more thermally-conductive post-like extensions with rounded ends designed to penetrate human hair or animal fur and touch the user's skin.

* * * * *